US 7,132,395 B1

(12) United States Patent
Greve et al.

(10) Patent No.: US 7,132,395 B1
(45) Date of Patent: *Nov. 7, 2006

(54) ANTIVIRAL METHODS USING HUMAN RHINOVIRUS RECEPTOR (ICAM-1)

(75) Inventors: Jeffrey M. Greve, Branford, CT (US); Alan McClelland, Old Saybrook, CT (US); Gary Davis, Milford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 242 days.

This patent is subject to a terminal disclaimer.

(21) Appl. No.: 08/316,384

(22) Filed: Sep. 30, 1994

Related U.S. Application Data

(63) Continuation of application No. 08/066,404, filed on May 21, 1993, now abandoned, which is a continuation of application No. 07/678,909, filed on Mar. 28, 1991, now abandoned, which is a continuation of application No. 07/390,662, filed on Aug. 10, 1989, now abandoned, which is a continuation-in-part of application No. 07/239,571, filed on Sep. 1, 1988, now abandoned, which is a continuation-in-part of application No. 07/262,428, filed on Oct. 25, 1988, now abandoned.

(51) Int. Cl.
*A61K 38/16* (2006.01)
*A61K 38/00* (2006.01)
*C07K 14/705* (2006.01)

(52) U.S. Cl. .............................. 514/8; 514/12; 530/350; 530/395

(58) Field of Classification Search ..................... 514/2, 514/8; 424/88, 184.1, 185.1, 198.1; 530/350, 530/395, 827, 868, 403; 435/69.3, 69.6, 69.7
See application file for complete search history.

(56) References Cited

U.S. PATENT DOCUMENTS

| 4,171,365 A | 10/1979 | Diana et al. |
| 4,209,526 A | 6/1980 | Diana et al. |
| 4,232,161 A | 11/1980 | Diana et al. |
| 4,234,725 A | 11/1980 | Diana et al. |
| 4,261,928 A | 4/1981 | Diana et al. |
| 4,372,976 A | 2/1983 | Diana |
| 4,427,653 A | 1/1984 | Springer |
| 4,451,476 A | 5/1984 | Diana |
| 4,843,087 A | 6/1989 | Diana |
| 4,956,281 A | 9/1990 | Wallner et al. |
| 5,081,228 A | 1/1992 | Dower et al. |
| 5,109,123 A | 4/1992 | Reinherz et al. |
| 5,179,017 A | 1/1993 | Axel et al. |
| 5,235,049 A | 8/1993 | McClelland et al. |
| 5,240,694 A | 8/1993 | Gwaltney, Jr. |
| 5,284,931 A | 2/1994 | Springer et al. ............ 424/85.8 |
| 5,304,636 A | 4/1994 | Blaas et al. ................. 530/350 |
| 5,324,510 A | 6/1994 | Wegner et al. |
| 5,340,800 A | 8/1994 | Liu et al. |
| 5,349,053 A | 9/1994 | Landolfi |
| 5,359,046 A | 10/1994 | Capon et al. |
| 5,372,933 A | 12/1994 | Zamarron et al. |
| 5,395,929 A | 3/1995 | Corbi et al. |
| 5,422,097 A | 6/1995 | Gwaltney |
| 5,472,849 A | 12/1995 | Rothlein et al. ........... 435/7.94 |
| 5,475,091 A | 12/1995 | Springer et al. |
| 5,525,487 A | 6/1996 | Gallatin et al. |
| 5,532,127 A | 7/1996 | Gallatin et al. |
| 5,580,969 A | 12/1996 | Hoke et al. |
| 5,589,453 A | * 12/1996 | Greve ......................... 514/8 |
| 5,597,567 A | 1/1997 | Whitcup et al. ......... 424/143.1 |
| 5,603,932 A | 2/1997 | Blaas et al. .............. 424/184.1 |
| 5,612,216 A | 3/1997 | Springer et al. |
| 5,663,293 A | 9/1997 | Gallatin et al. |
| 5,674,982 A | 10/1997 | Greve et al. |
| 5,686,581 A | 11/1997 | Greve et al. ................ 530/402 |
| 5,686,582 A | 11/1997 | Greve et al. |
| 5,712,245 A | 1/1998 | Blaas et al. ..................... 514/2 |
| 5,730,983 A | 3/1998 | Wegner et al. ........... 424/185.1 |
| 5,821,341 A | 10/1998 | McClelland et al. ..... 530/388.2 |
| 5,831,036 A | 11/1998 | Springer et al. ............. 530/395 |
| 5,849,699 A | 12/1998 | McClelland et al. .......... 514/12 |
| 5,859,212 A | 1/1999 | McClelland et al. ........ 530/413 |
| 5,871,733 A | 2/1999 | Greve et al. ............. 424/134.1 |
| 5,879,712 A | 3/1999 | Bomberger et al. ......... 424/489 |
| 6,051,231 A | 4/2000 | Greve ...................... 424/185.1 |
| 6,096,862 A | 8/2000 | Greve et al. ................ 530/324 |
| 6,107,461 A | 8/2000 | Greve et al. ................ 530/350 |
| 6,130,202 A | * 10/2000 | Greve et al. |
| 6,143,298 A | 11/2000 | Greve et al. ............. 424/185.1 |
| 6,514,936 B1 | * 2/2003 | Greve et al. |

FOREIGN PATENT DOCUMENTS

| AU | A-14630/88 | 10/1988 |
| AU | 1551888 | 11/1988 |
| AU | 2633288 | 5/1989 |
| AU | 623105 | 6/1989 |
| AU | B-48767/90 | 2/1990 |
| AU | 637324 | 3/1990 |
| AU | 5129990 | 9/1990 |
| AU | 623105 | 5/1992 |
| AU | 637324 | 5/1993 |
| AU | 641134 | 9/1993 |
| AU | 652567 | 9/1994 |
| AU | 675441 | 2/1997 |
| CA | 1339193 | 8/1997 |
| DE | 3712678 A1 | 10/1988 |
| EP | 0169146 A3 | 1/1986 |
| EP | 0169146 | 1/1986 |

(Continued)

OTHER PUBLICATIONS

Rothlein, R. et al. J. Immunol 137: 1270–1274. Aug. 15, 1986. A human intercellular adhesion molecule, (ICAM–1)...*

(Continued)

*Primary Examiner*—Phillip Gambel
(74) *Attorney, Agent, or Firm*—Barbara A. Shimei

(57) ABSTRACT

Method of inhibiting human rhinovirus (HRV) Infection by contacting said HRV with a polypeptide comprising a fragment of human rhinovirus major receptor (HRR), said fragment comprising the HRV binding site and being selected from a specific group consisting of HRR domains.

19 Claims, 7 Drawing Sheets

FOREIGN PATENT DOCUMENTS

| | | |
|---|---|---|
| EP | 0169729 A2 | 1/1986 |
| EP | 0192175 A2 | 8/1986 |
| EP | 0207453 A2 | 1/1987 |
| EP | 0227604 A2 | 7/1987 |
| EP | 0261403 A2 | 3/1988 |
| EP | 0280578 A2 | 8/1988 |
| EP | 0287076 B1 | 10/1988 |
| EP | 0289949 | 11/1988 |
| EP | 0289949 A2 | 11/1988 |
| EP | 0314863 A2 | 5/1989 |
| EP | 0319815 | 6/1989 |
| EP | 0319815 A2 | 6/1989 |
| EP | 0380068 A1 | 1/1990 |
| EP | 0362526 A2 | 4/1990 |
| EP | 0362531 A1 | 4/1990 |
| EP | 0365837 A2 | 5/1990 |
| EP | 0379904 A1 | 8/1990 |
| EP | 0387701 B1 | 9/1990 |
| EP | 0391088 A2 | 10/1990 |
| EP | 0459577 A2 | 12/1991 |
| EP | 0468257 | 1/1992 |
| EP | 0510483 | 10/1992 |
| EP | 0566554 | 10/1993 |
| EP | 0319815 | 8/1994 |
| EP | 0379904 | 5/1996 |
| EP | 0287076 | 10/1998 |
| EP | 0488061 | 11/1998 |
| FI | 100601 | 1/1998 |
| GB | 2022826 | 12/1979 |
| IE | 74144 | 7/1997 |
| IL | 91454 | 8/1995 |
| KR | 202435 | 6/1999 |
| NZ | 230474 | 8/1989 |
| NZ | 232203 | 1/1990 |
| PT | 92920 | 7/1990 |
| PT | 91570 | 11/1994 |
| SA | 90/0469 | 10/1990 |
| TW | 52785 | 11/1991 |
| TW | 52785 | 3/1992 |
| WO | WO 88/06592 | 9/1988 |
| WO | WO 89/10938 | 11/1989 |
| WO | 0364690 A2 | 4/1990 |
| WO | WO 90/03400 | 4/1990 |
| WO | 0387668 A1 | 9/1990 |
| WO | WO 90/10646 | 9/1990 |
| WO | WO 90/10652 | 9/1990 |
| WO | WO 90/13316 | 11/1990 |
| WO | WO 91/16927 | 11/1991 |
| WO | WO 91/16928 | 11/1991 |
| WO | WO 91/18010 | 11/1991 |
| WO | WO 91/18011 | 11/1991 |
| WO | 9201049 | 1/1992 |
| WO | 9206119 | 4/1992 |
| WO | 9212994 | 8/1992 |
| WO | 9306842 | 4/1993 |
| WO | 9306850 | 4/1993 |
| WO | 9313210 | 7/1993 |
| WO | 9400485 | 1/1994 |
| WO | 9401553 | 1/1994 |
| WO | 9411400 | 5/1994 |
| WO | 9527736 | 10/1995 |
| WO | 9528170 | 10/1995 |
| WO | 9603142 | 2/1996 |
| WO | 9606622 | 3/1996 |
| WO | 9627292 | 9/1996 |
| WO | 9634015 | 10/1996 |
| WO | 9640069 | 12/1996 |
| ZA | 896668 | 6/1990 |
| ZA | 900469 | 10/1990 |

OTHER PUBLICATIONS

Tomassini, J.E. et al. J. Virol. 58(2) 290–295. May 1986 Isolation of a receptor protein . . .*

Ruoslahti, E. et al. in Synthetic Peptides in Biol. and Medicine, Alitalo, K. et al (ed.), 1985 Elsevier, N.Y.*

Dustin, M. L. et al. J. Immunol. 137(1):245–254. Jul. 1, 1986 Induction by IL–1 . . .*

Marlin, S. D. et al. Cell 51:813–819. Dec. 4, 1987. Purified Intercell. Adhes. Mol.–1 (ICAM–1) is a ligand. . .*

Abraham, G. and R.J. Colonno, "Many Rhinovirus Serotypes Share the Same Cellular Receptor", J. Virol. 51:340–345.

Colonno, R.J. and J.E. Tomassini, "Viral Receptors: A Novel Approach for the Prevention of Human Rhinovirus Infection", in *Medical Virology VI*, de la Maza, L.M. and E.M. Peterson, eds. (Elsevier, New York, 1987), pp. 331–351.

Colonno, R.J., P.L. Callahan, and W.J. Long, "Isolation of a Monoclonal Antibody That Blocks Attachment of the Major Group of Human Ehinoviruses", J. Virol. (1986) 57(1):7–12.

Ginsberg, M., M.D. Pierschbacher, E. Ruoslahti, G. Marguerie, and E. Plow, "Inhibition of Fibronectin Binding to Platelets by Proteolytic Fragments and Synthetic Peptides Which Support Fibroblast Adhesion", J. Biol. Chem. (1985) 260(7):3931–3936.

Medical Microbiology: An Introduction to Infectious Diseases, 2d ed., J.C. Sherris, ed. (Elsevier Science Publishing Co., Inc., NY 1990), pp. 514–515.

Tomassini, J.E. and R.J. Colonno, "Isolation of a Receptor Protein Involved in Attachment of Human Rhinoviruses", J. Virol. 58(2):290–295.

Winther, B., J.M. Gwaltney, Jr., N. Mygind, R.B. Turner, and J.O. Hendley, "Sites of Rhinovirus Recovery After Point Inoculation of the Upper Airway", JAMA (1986) 256(13):1763–1767.

Hsiung, G.D., Chapter 14 "Picornaviridae", in *Hsiung Diagnostic Virology*, Fourth Edition, Hsiung, G. D., C. K. Y. Fong, and M. L. Landry, eds., (Yale University Press, New Haven , 1994), pp. 119–140.

Abraham, G. and R.J. Colonno, "Characterization of human rhinoviruses displaced by an anti–receptor monoclonal antibody", J. Virol.62(7):2300–2306 (Jul. 1988).

Ashkenazi, A., L.G. Presta, S.A. Marsters, T.R. Camerato, K.A. Rosen, B.M. Fendly, and D.J. Capon, "Mapping the CD4 binding site for human immunodeficiency virus by alanine scanning mutagenesis", Proc. Natl. Acad. Sci. USA 87:7150–7154 (Sep. 1990).

Brodsky, M.H., M.Warton, R.M. Myers, and D.R. Littman, "Analysis of the site in CD4 that binds to the HIV envelope glycoprotein", J. Immunol. 144(8):3078–3086 (Apr. 1990).

Callahan, P.L., S. Mizutani, and R.J. Colonno, "Molecular cloning and complete sequence determination of RNA genome of human rhinovirus type 14", Proc. Natl. Acad. Sci. USA 82(3):732–6 (Feb. 1985).

Colonno, R.J., "Virus receptors: the Achilles' heel of human rhinoviruses", in Innovations in Antiviral Development and the Detection of Virus Infection, T. Block et al., eds., (Plenum Press, NY, 1992), pp. 61–70.

Colonno, R.J., P.L. Callahan, D.M. Leippe, R.R. Rueckert, and J.E. Tomassini, "Inhibition of rhinovirus attachment by neutralizing monoclonal antibodies and their Fab fragments," J. Virol. 63(1):36–42 (Jan. 1989).

Colonno, R.J., "Cell surface receptors for picornaviruses", Bioassays 5(6):270–4 (1986).

Colonno, R.J., "Molecular interactions between human rhinoviruses and their cellular receptors", Seminars in Virol. 3(2):101–107 (1992).

Colonno, R.J., R.L. LaFemina, C.M. DeWitt, and J.E. Tomassini, "The major–group rhinoviruses utilize the intercellular adhesion molecule 1 ligand as a cellular receptor during infection", in *New Aspects of Positive–Strand RNA Viruses*, Second International Symposium, Vienna, Austria, Meeting Date 1989, Brinton et al., eds. (Am. Soc. Microbiol., Washington, DC, 1990), pp. 257–261.

Colonno, R.J., G. Abraham, and J.E. Tomassini, "Molecular and biochemical aspects of human rhinovirus attachment to cellular receptors", in *Molecular Aspects of Picornavirus Infection and Detection*, [Presentations ICN–UCI Int. Conf. Virol.], Meeting Date 1988, Semler et al., eds. (Am. Soc. Microbiol., Washington, DC, 1989), pp. 169–178.

Colonno, R.J., J.E. Tomassini, P.L. Callahan, and W.J. Long, "Characterization of the cellular receptor specific for attachment of most human rhinovirus serotypes", in *Virus Attachment Entry Cells*, Proc. ASM Conf., Meeting Date 1985, Crowell et al., eds. (Am. Soc. Microbiol. Washington, DC, 1986), pp. 109–115.

Colonno, R.J., "Molecular interactions between human rhinoviruses and the adhesion receptor ICAM– 1", *in Microb. Adhes. Invasion*, [Proc. Symp.], meeting date 1990, Hook et al., eds. (Springer, NY, 1992), pp. 33–41.

Colonno, R.J., J.H. Condra, and S. Mizutani, "Interaction of cellular receptors with the canyon structure of human rhinoviruses", in *UCLA Symposia on Molecular and Cellular Biology New Series, vol. 90, Cell Biology of Virus Entry, Replication, and Pathogenesis*, Taos, NM, Feb. 28–Mar. 5, 1988, Compans et al., eds. (Alan R. Liss, Inc., NY, 1988) pp. 75–84.

Colonno, R.J., R. B. Register, D.W. Lineberger, and C.R. Uncapher, "Identification of ICAM–1 residues critical for attachment of human rhinoviruses", Meeting on Molecular Biology of Human Pathogenic Viruses held at the 20$^{th}$ Annual Meeting of the Keystone Symposia on Molecular and Cellular Biology, Lake Tahoe, CA, Mar. 8–15, 1991, J. Cell Biochem. Suppl. 15(Part E):82, #M310 (1991).

Colonno, R.J., J.H. Condra, S. Mizutani, G. Abraham, P.L. Callahan, J.E. Tomassini, and M.A. Murcko, "Evidence for direct involvement of the rhinovirus canyon with cellular receptors", in *Symposium on Cell Biology of Virus Entry, Replication and Pathogenesis, Positive Strand RNA Viruses*, 17$^{th}$ Annual UCLA meeting on Molecular and Cellular Biology, Taos, NM, Feb. 28–Mar. 5, 1988, J. Cell. Biochem. Suppl., 0 (12 Part C):4, #J005 (1988).

Colonno, R.J., J.E. Tomassini, and P.L. Callahan, "Isolation and characterization of a monoclonal antibody which blocks attachment of human rhinoviruses", in *UCLA Symposia on Molecular and Cellular Biology*, New Series, vol. 54, Positive Strand RNA Viruses, Keystone, CO Apr. 20–26, 1986, Brinton et al., eds. (Alan R. Liss, Inc., NY, 1987), pp. 93–102.

Colonno, R.J., J.E. Tomassini, and P.L. Callahn, "Human rhinovirus attachment requires a specific cellular receptor protein", in *Symposium on Positive Strand RNA Viruses*, 15$^{th}$ Annual Meeting of the UCLA Symposia on Molecular and Cellular Biology, Apr. 20–26, 1986, J. Cell. Biochem Suppl., 0 (10 Part D):266, #Q4 (1986).

Condra, J.H., V.V. Sardan, J.E. Tomassini, A.J. Schlabach, M.–E. Davies, D.W. Lineberger, D.J. Graham, and R.J. Colonno,, "Bacterial expression of antibody fragments that block human rhinovirus infection of cultured cells", J. Biol. Chem. 265(4):2292–2295 (Feb. 1990).

Cordingley, M.G., P.L. Callahan, V.V. Sardana, V.M. Garsky, and R.J. Colonno, "Substrate requirements of human rhinovirus 3C protease for peptide cleavage in vitro", J. Biol. Chem. 265(16):9062–5 (1990).

Cordingley, M.G., R.B. Register, P.l. Callahan, V.M. Garsky, and R.J. Colonno, "Cleavage of small peptides in vitro by human rhinovirus 14 3C protease expressed in *Escherichia coli*", J. Virol. 63(12):5037–45 (Dec. 1989).

Dewalt, P.G., M.A. Lawson, R.J. Colonno, and B.L. Semler, "Chimeric picornavirus polyproteins demonstrate a common 3C proteinase substrate specificity", J. Virol. 63(8):3444–3452 (1989).

Dick, E.C., and C.R. Dick, "Natural and Experimental Infections of Nonhuman Primates with Respiratory Viruses", Laboratory Animal Science 24(1): 177–181 (1974).

Emini, E.A., W.A. Schleif, R.J. Colonno, and E.Wimmer, "Antigenic conservation and divergence between the viral–specific proteins of poliovirus type 1 and various picornaviruses", Virol. 140(1):13–20 (1985).

Hazuda, D., V. Sardana, P. Callahan, M. Cordingley, and R. Colonno, "Chemical approaches to mapping the active site thiol of human rhinovirus 3C protease", Joint Meeting of the American Society for Biochemistry and Molecular Biology and the American Association of Immunologists, New Orleans, LA, Jun. 4–7, 1990, Fed. Am. Soc. Exp. Biol. J. 4(7):#1605 (1990).

Johnston, S.C., M.L. Dustin, M.L. Hibbs, and T.A. Springer, "On the species specificity of the interaction of LFA–1 with intercellular adhesion molecules", J. Immunol. 145(4):1181–1187 (Aug. 1990).

Lamarre, D., D.J. Capon, D.R. Karp, T.Gregory, E.O. Long, and R.–P. Sekaly, "Class II MHC molecules and the HIV envelope glycoprotein interact with functionally distinct regions of the molecule", EMBO J. 8(11):3271–3277 (1989).

Lineberger, D.W., C.R. Uncapher, D.J. Graham, and R.J. Colonno, "Domains 1 and 2 of ICAM–1 are sufficient to bind human rhinoviruses", Virus Research 24(2): 173–86 (1992).

Maddon, P.J., A.G. Dalgleish, J.S. McDougal, P.R. Clapham, R.A. Weiss, and R. Axel, "The T4 Gene Encodes the AIDS Virus Receptor and is Expressed in the Immune System and the Brain", Cell 47: 333–348 (Nov. 1986).

Mendelsohn, C.L., E. Wimmer, and V.R. Racaniello, "Cellular receptor for poliovirus: molecular cloning, nucleotide sequence, and expression of a new member of the immunoglobulin superfamily", Cell 56:855–865 (Mar. 1989).

Mizutani, S., and R.J. Colonno, In vitro synthesis of an infectious RNA from cDNA clones of human rhinovirus type 14:, J. Virol. 56(2):628–32 (Nov. 1985).

Register, R.B., C.R. Uncapher, A.M. Naylor, D.W. Lineberger, and R.J. Colonno, "Human–murine chimeras of ICAM–1 identify amino acid residues critical for rhinovirus and antibody binding", J. Virol. 65(12):6589–6596 (Dec. 1991).

Rueckert, R. B. Sherry, A. Mosser, R. Colonno, and M. Rossman, "Location of four neutralization antigens on the three–dimensional surface of a common–cold picornavirus, human rhinovirus 14", in *Virus Attachment Entry Cells*, Proc. ASM Conf., Meeting date 1985, Crowell et al., eds. (Am. Soc. Microbiol., Washington, DC, 1986), pp. 21–27.

Sherry, B., A.G. Mosser, R.J. Colonno, and R.R. Rueckert, "Use of monoclonal antibodies to identify four neutralizing immunogens on a common cold picornavirus, human rhinovirus 14", J. Virol. 57(1):246–57 (Jan. 1986).

Tomassini, J.E., T.R. Maxson, and R.J. Colonno, "Biochemical characterization of a glycoprotein required for rhinovirus attachment", J. Biol. Chem. 264(3):1656–1662 (Jan. 1989).

Tomassini, J.E., and R.J. Colonno, "Isolation and characteriation of a cellular receptor involved in attachment of human rhinoviruses to cells", in *Symposium on Positive Strand RNA Viruses*, 15$^{th}$ Annual Meeting of the UCLA Symposia on Molecular and Cellular Biology, Apr. 20–26, 1986, J. Cell. Biochem. Suppl., 0 (10 Part D):300, #Q92 (1986).

Abraham, G. and Colonno, R. J., "Many Rhinovirus Serotypes Share the Same Cellular Receptor", J. Virol. 51:340–345 (1984).

Anasetti et al., "Activation of Natural Killer Cells by LFA–3 Binding to CD2", Publication, Fred Hutchinson Cancer Research Center, Seattle WA, and Molecular Diagnostics, West Haven, CT (U.S.A.).

Argenbright et al., "Monoclonal Antibodies to the Leukocyte Membrane CD18 Glycoprotein Complex and to Intercellular Adhesion Molecule–1 Inhibit Leukocyte–Endothelial Adhesion in Rabbits", J. Leukoc. Biol. 49:253–257 (1991).

Argenbright, L. W. and Barton, R. W., "Interactions of Leukocyte Integrins with Intercellular Adhesion Molecule–1 in the Production of Inflammatory Vascular Injury In Vivo: the Shwartzman Reaction Revisited", J. Clin. Invest. 89(1):259–272 (1992).

Badger et. al., "Structure Analysis of a Series of Antiviral Agents Complexed with Human Rhinovirus 14", PNAS 85:3304–3308 (1988).

Bangham, C. R. M. and McMichael, A. J., "Nosing ahead in the cold war" Nature 334:16 (1990).

Bebbington, C. R., and Hentschel, C. C. G. "The use of vectors based on gene amplification for the expression of cloned genes in mammalian cells" DNA Cloning 3:163–186 (1987).

Blann, A. D., "Cell Hybrids: an important new source of antibody production" Med. Lab. Sci. 36:329–338 (1979).

Bock et al., "Characterization of soluble forms of NCAM", FEBS Lett 225(1,2):33–36 (1987).

Bowie et al., "Deciphering the Message in Protein Sequences: Tolerance to Amino Acid Substitutions", Science 247:1306–1310 (1990).

Campbell, B. A. and Cords, C. E., "Monoclonal Antibodies That Inhibit Attachment of Group B Coxsackieviruses", J. Virol. 48(2):561–564 (1983).

Capon et al., "Designing CD4 immunoadhesins for AIDS therapy", Nature 337:525–531 (1989).

Cate et al., "Isolation of the Bovine and Human Genes for Müllerian Inhibiting Substance and Expression of the Human Gene in Animal Cells", Cell 45:685–698 (1986).

Cole et al., "Topographic Localization of the Heparin–binding Domain of the Neural Cell Adhesion Molecule N–CAM", J. Cell Biol. 103:1739–1744 (1986).

Colonno et al., "Isolation of a Monoclonal Antibody that Blocks Attachment of the Major Group of Human Rhinoviruses", J. Virology 57:7–12 (1986).

Colonno, R. J. and Tomassini, J. E., "Viral Receptors: A Novel Approach For The Prevention Of Human Rhinovirus Infection", in *Medical Virology VI*, de la Maza, L. M. and E. M. Peterson, eds. (Elsevier, New York, 1987) 331–351.

Cooper, G.M., "Cellular Transforming Genes", Science 217: 801–806 (1982).

Couch, R.B., "Rhinoviruses", *Virology*, Second Edition, edited by B. N. Fields, D. M. Knipe et al. Raven Press, Ltd., New York, 607–629 (1990).

Couch et al., "Effect of Route Inoculation on Experimental Respiratory Viral Disease in Volunteers and Evidence for Airborne Transmission", Bacteriol. Rev. 30:517–529 (1966).

Creighton, T.E., *Proteins* by W. H. Freeman and Company, New York, 33–34 (1984).

Crump et al., "In Vitro Inhibitory Activity of Soluble ICAM–1 for the Numbered Serotypes of Human Rhinovirus", Antiviral Chemistry and Chemother. 4(6):323–327 (1993).

Cunningham et al., "Neural Cell Adhesion Molecule: Structure, Immunoglobulin–Like Domains, Cell Surface Modulation, and Alternative RNA Splicing", Science 236:799–806 (1987).

Cybulsky, M. I. and Gimbrone, Jr., M. A., "Endothelial Expression of a Mononuclear Leukocyte Adhesion Molecule During Atherogenesis", Science 251:788–791 (1991).

D'Alessio et al., "Short–Duration Exposure and the Transmission of Rhinoviral Colds", J. Inf. Dis. 150(2):189–193 (1984).

Deen et al., "A Soluble Form of CD4 (T4) Protein Inhibits AIDS Virus Infection", Nature 331:82–86 (1988).

Dick, E.C., "Experimental Infection of Chimpanzees with Human Rhinovirus Types 14 and 43", Proceedings Of The Society For Experimental Biology And Medicine 127:1079–1081 (1968).

Dochez et al., "Studies in the Common Cold. IV. Experimental Transmission of the Common Cold to Anthropoid Apes and Human Beings by Means of a Filtrable Agent", J. Exp. Med. 52:701–716 (1930).

Douglas et al., "Prophylactic Efficacy of Intranasal Alpha 2–Interferon Against Rhinovirus Infections in the Family Setting", The New England J. of Med. 314:65–70 (1986).

Douglas, R. G., "Pathogenesis of Rhinovirus Common Colds in Human Volunteers", Annals of Otology, Rhinology and Laryngology 79:563–571 (1970).

Dustin et al., "Induction by IL 1 and Interferon–$\gamma$: Tissue Distribution, Biochemistry, and Function of a Natural Adherence Molecule (ICAM–1)", J. Immnol. 137(1):245–254 (1986).

Dustin et al., "Supergene Families Meet in the Immune System" Immunology Today, 9(7 and 8):213–215 (1988).

Dustin et al., "Correlation of CD2 Binding and Functional Properties of Multimeric and Monomeric Lymphocyte Function–Associated Antigen 3", J. Exp. Med. 169:503–517 (1989).

Ey, P.L., et. al.,"Isolation of Pure IgG1, IgG2a, and IgG2b Immunoglobulins from Mouse Serum Using Protein A–Sepharose", Immunochemistry 15:429–436 (1978).

Fisher et al., "HIV Infection is Blocked in vitro by Recombinant Soluble CD4", Nature 331:76–78 (1988).

Fox et al., "Prevention of a Rhinovirus and Poliovirus Uncoating by WIN 51711, a New Antiviral Drug", Antimicrob. Ag. and Chemotherapy 30:110–116 (1986).

Galfrey et. al., "Antibodies to Major Histocompatibility Antigens Produced by Hybrid Cell Lines", Nature 266:550–552 (1977).

Gething, M.J. and Sambrook, J., "Construction of Influenza Haemagglutinin Genes that Code for Intracellular and Secreted Forms of the Protein" Nature 300:598–603 (1982).

Ginsberg et al., "Inhibition of Fibronectin Binding to Platelets by Proteolytic Fragments and Synthetic Peptides Which Support Fibroblast Adhesion", J. Biol. Chem. 260(7): 3931–3936 (1985).

Giranda et al., "Modeling of the Human Intercellular Adhesion Molecule–1, the Human Rhinovirus Major Group Receptor" Proteins: Structure, Function, and Genetics, 7:227–233 (1990).

Gough, N., "Putting A Stop To An Immunogobulin Message", Trends Genet. 3(9):238–240 (1987).

Gower et al., "Alternative Splicing Generates a Secreted Form of N–CAM in Muscle and Brain", Cell 55:955–964 (1988).

Graham, F.L., and Van der Eb, A. J., "A New Technique for the Assay of Infectivity of Human Adenovirus 5 DNA", Virology 52: 456–467 (1973).

Green et al., "Immunogenic Structure of the Influenza Virus Hemagglutinin", Cell 28:477–487 (1982).

Greve et al., "The Major Human Rhinovirus Receptor Is ICAM–1", Cell 56:839–847 (1989).

Greve et al., "Mechanisms of Receptor–Mediated Rhinovirus Neutralization Defined by Two Soluble Forms of ICAM–1", J. Virology 65:6015–6023 (1991).

Gross–Bellard et al., "Isolation of High–Molecular–Weight DNA from Mammalian Cells", Eur. J. Biochem. 36:32–38 (1973).

Güssow, D. and Ploegh, H., "Soluble class I antigens: a conundrum with no solution?", Immunology Today 8(7, 8):220–222 (1987).

Gwaltney et al., *Diagnostic Procedures for Viral, Rickettsial and Chlamydial Infections*, N. J. Schmidt and R. W. Evans, Eds, 6th edition. pp. 603, Am Pub. Health. Assoc., Washington D.C. (1989).

Halperin et al., "Exacerbations of Asthma in Adults During Experimental Rhinovirus Infection", Am. Rev. Respir. Dis. 132:976–980 (1985).

Hamparian et al., "A Collaborative Report: Rhinoviruses–Extension of the Numbering System from 89 to 100", Virology 159:191–192 (1987).

Hardy et al., "Intrnasal Drug Delivery by Spray and Drops", J. Pharm. Pharmacol. 37:294–297 (1985).

Hayden et al., "Safety and Efficacy of Intranasal Pirodavir (R77975) in Experimental Rhinovirus Infection", Antimicrob. Agents Chemother. 36(4):727–732 (1992).

Hayden et al., "Prevention of Natural Colds by Contact Prophylaxis with Intranasal Alpha2–Interferon", The New England Journal of Medicine, 314(2):71–75 (1986).

Hayden et al., "Modification of Experimental Rhinovirus Colds by Receptor Blockade" Antiviral Research 9:233–247 (1988).

Helenius, A. and Von Bonsdorff, C. H., "Semliki Forest Virus Membrane Proteins, Preparation and Characterization of Spike Complexes Soluble in Detergent–Free Medium" Biochimica et Biophysica Acta 436:895–899 (1976).

Hendley et al., "Relation Between Naturally acquired Immunity and Infectivity of Two Rhinoviruses in Volunteers", J. Inf. Dis. 125:243–248 (1972).

Holland, J. J. and McLaren, L. C., "The mammalian cell–virus relationship. II. Absorption, Reception and Eclipse of Poliovirus by HeLa Cells" J. Exp. Med. 109:487–504 (1959).

Holland, J. J., "Receptor affinities as Major Determinants of Enterovirus Tissue Tropisms in Humans", Virology 15:312–326.

Horton et al., "Gene Splicing by Overlap Extension: Tailor–Made Genes Using the Polyerase Chain Reaction", Bio-Techniques 8(5):528–535 (1990).

Hussey et. al., "A Soluble CD4 Protein Selectively Inhibits HIV Replication and Syncytium Formation" Nature, 331:78–81 (1988).

Illum, L., "The Nasal Delivery of Peptides and Proteins", Trends in Biotech. 9:284–289 (1991).

Johnston et al., "Viruses as Precipitants of Asthma Symptoms. III. Rhinoviruses: Molecular Biology and Prospects for Future Intervention", Clin. Exp. Allergy, 23:237 (1993).

Johnston et al., "Viral Infections in Exacerbations in School Children with Cough or Wheeze: A Longitudinal Study", Am. Rev. Resp. Dis., 145:A546 (1992).

Kamarck, M. E., and Ruddle, F. H., "Somatic Cell Genetics and the Human Gene Map", Chapter 105 in *Handbook of Experimental Immunology in Four Volumes, vol. 3: Genetics and Molecular Immunology*, D. M. Weir, ed. (Blackwell Scientific Publications, Boston, MA, 1986).

Katz et al., "Chromosome Mapping of Cell Membrane Antigens Expressed on Activiated B Cells", Eur. J. Immunol., 15:103–106 (1985).

Kavenoff, R., and Zimm, B. H., "Chromosome–Sized DNA Molecules from Drosophila", Chromosoma (Berl.) 41:1–27 (1983).

Kühn et al., "Gene Transfer, Expression, and Molecular Cloning of the Human Transferrin Receptor Gene", Cell 37:95–103 (1984).

Lebman et al., "A Monoclonal Antibody that Detects Expression of Transferrin Receptor in Human Erythroid Precursos Cells", Blood 59(3):671–678 (1982).

Lemanske et al., "Rhinovirus Upper Respiratory Infection Increases Airway Hyperreactivity and Late Asthmatic Reactions", J. Clin. Invest. 83:1–10 (1989).

Littlefield, J.W., "Selection of Hybrids from Matings of Fibroblasts in vitro and Their Presumed Recombinants", Science 145:709–710 (1964).

Lonberg–Holm et al., "Unrelated Animal Viruses Share Receptors", Nature 259:679–681 (1976).

Margulies, D. H., et. al., "Engineering Soluble Major Histocompatibility Molecules: Why and How", Immunol. Res. 6: 101–116 (1987).

Marlin, S.D. and Springer, T. A., "Purified Intercellular Adhesion Molecule–1 (ICAM–1) Is a Ligand for Lymphocyte Function–Associated Antigen 1 (LFA–1)", Cell 51:813–819 (1987).

Marlin et al., "A Soluble Form of Intercellular Adhesion Molecule–1 Inhibits Rhinovirus Infection", Nature 344:70–72 (1990).

Marsh et al., "Antibody–toxin Conjugation", *Immunotoxins* by Kluwer Academic Publishers, Boston, Dordrecht, Lancaster 213–237 (1988).

Marsh et al., "Interactions of Semliki Forest Virus Spike Glycoprotein Rosettes and Vesicle with Cultures Cells", J. Cell Biology 96:455–461 (1983).

McClelland et al., "Identification of Monoclonal Antibody Epitopes and Critical Residues for Rhinovirus in Domain 1 of ICAM–1", PNAS 88(18):7993–7997 (1991).

McCray, J. and Werner, G., "Different Rhinovirus Serotypes Neutralized by Antipeptide Antibodies", Nature 329:736–738 (1987).

Medical Microbiology: "An Introduction to Infectious Diseases", 2nd ed., J.C. Sherris, ed. (Elsevier Science Publishing Co., Inc., N.Y. 1990) pp. 514–515.

Medrano, L. and Green, H., "Picornavirus Receptors and Picornavirus Multiplication in Human–Mouse Hybrid Cell Lines", Virology 54:515–524 (1973).

Melchers et al., *Lymphocyte Hybridomas*, vol. 81 of Current Topics in Microbiology and Immunology, W. Arber, W. Henle, P.H. Hofschneider, J.H. Humphrey, J. Klein, P. Koldovsky, H. Koprowski, O. Maaloe, F. Melchers, R. Rott, H.G. Schweiger, L. Syrucek, P.K. Vogt, eds (Springer Verlang, New York, 1978).

Mendelsohn et al., "Transformation of a Human Poliovirus Receptor Gene into Mouse Cells", PNAS 83:7845–7849 (1986).

Minor, P.D., "Growth, Assay and Purification of Picornaviruses", in *Virology: A Practical Approach*, B.W.J. Mahy, ed. (IRL Press Limited, Oxford, England), 25–41 (1985).

Minor et al., "Monoclonal antibodies which block cellular receptors of poliovirus", Virus Research 1:203–232 (1984).

Morein, B., "Potentiation of the Immune Respose by Immunization with Antigens in Defined Multimeric Physical Forms", Veterinary Immunology and Immunopathology 17:153–159 (1987).

Niman et al., "Anti–peptide antibodies detect oncogene–related proteins in urine", PNAS 82:7924–7928 (1985).

Nobis et al., "Production of a Monoclonal Antibody against an Epitope on HeLa Cells that Is the Functional Poliovirus Binding Site", J. Gen. Virol. 66:2563–2569 (1985).

Ohlin et al., "Spectrum of Activity of Soluble Intercellular Adhesion Molecule–1 Against Rhinovirus Reference Strains and Field Isolates", Antimicrob. Agents and Chemother. 38:1413–1415 (1994).

Parham, P., "Monoclonal Antibodies Against HLA Products and Their use in Immunaffinity Purification," Methods in Enzymology 92:110–138 (1983).

Pepinsky et al., "The Increased Potency of Crossed–linked Lymphocyte Function–associated Antigen–3 (LFA–3) Multimers Is a Direct Consequence of Changes in Valency", J. Biol. Chem. 266(27):18244–18249 (1991).

Peterson, A. and Seed, B., "Genetic Analysis of Monoclonal Antibody and HIV Binding Sites on the Human Lymphocyte Antigen CD4", Cell 54:65–72 (1988).

Rossman et al., "Structure of a Human Common Cold Virus and Functional Relationship to other Picornaviruses", Nature 317: 145–153 (1985).

Rothlein et al., "A Form of Circulating ICAM–1 In Human Serum", J. Immuno. 147(11):3788–3793 (1991).

Rothlein et al., "A Human Intercellular Adhesion Molecule (ICAM–1) Distinct From LFA–1", J. Immuno. 137(4):1270–1274 (1986).

Ruddle et al., "DNA–Mediated Gene Transfer in Mammalian Gene Cloning", Genetic Engineering 6:319–338 (1984).

Ruoslahti et al., "Synthetic Peptides in the Analysis of Cell Adhesion," in *Synthetic Peptides in Biology and Medicine* Elsevier Science Publishers, pp. 191–197 (1985).

Saiki et al., "Enzymatic Amplification of β–Globin Genomic Sequences and Restriction Site Analysis for Diagnosis of Sickle Cell Anemia," Science 230:1350–1354 (1985).

Sambrook et al., *Molecular Cloning: A Laboratory Manual*, 2d ed. (Clold Spring Harbor Laboratory Press, Cold Spring Harbor, NY, 1989) pp. 1.21–1.52.

Schipper et al., "The Nasal Mucocilliary Clearance: Relevance to Nasal Drug Delivery", Pharm. Res. 8:807–814 (1991).

Scopes, R.K., "Separation By Precipitation," in *Protein Purification: Principles & Practice* (1982) Springler Verlag, NY, pp. 39–46.

Seed, B. and Aruffo, A., "Molecular Cloning of the CD2 antigen, the T–Cell Erythrocyte Receptor, by a Rapid Immunoselection Procedure," PNAS 84:3365–3369 (1987).

Seed, B., "An LFA–3 cDNA Encodes a Phospholipid–Linked Membrane Protein Homologous to its Receptor CD2," Nature 329: 840–842 (1987).

Seth et al., "Circulating ICAM–1 Isoforms: Diagnostic Prospects for Inflammatory and Immune Disorders," Lancet 338:83–84 (1991).

Sherman–Gold, R., "Companies Pursue Therapies Based on Complex Cell Adhesion Molecules", Genetic Engineering News pp. 6–7,14 (Jul. 1993).

Sherry, B. and Rueckert, R., "Evidence for at Least Two Dominant Neutralization Antigens on Human Rhinovirus 14," J. Virol. 53(1):127–143 (1985).

Shih, C. and Weinberg, R. A., "Isolation of a Transforming Sequence from a Human Bladder Carcinoma Cell Line," Cell 29: 161–169 (1982).

Siddique et al., "The Poliovirus Sensitivity (PVS) Gene Is on Chromosome 19q12–>q13.2", Genomics 3:156–160 (1988).

Simmons et al., "ICAM, an Adhesion Ligand of LFA–1, is Homologous to the Neural Cell Adhesion Molecule NCAM," Nature 331:624–627 (1988).

Simons et al., "Formation of Protein Micelles from Amphiphilic Membrane Proteins", PNAS 75(11):5306–5310 (1978).

Skerra, A. and Pluckthun, A., "Assembly of a Functional Immunoglobulin FV Fragment in *Escherichia coli*" Science, 240: 1038–1041 (1988).

Smith, T.J., et. al., "The Site of Attachment in Human Rhinovirus 14 for 4 Antiviral Agents that Inhibit Uncoating", Science 233:1286–1293 (1986).

Smith et al., "Blocking of HIV–1 Infectivity by a Soluble, Secreted Form of the CD4 Antigen," Science 238:1704–1707 (1987).

Smith et al., "Modification and Secretion of Human Interleukin 2 Produced in Insect Cells by a Baculovirus Expression Vector", PNAS 82:8404–8408 (1985).

Springer, T.A., "Adhesion Receptors of the Immune System", Nature 346:425–434 (1990).

Staunton et al., "Primary Structure of ICAM–1 Demonstrates Interaction between Members of the Immunoglobulin and Integrin Supergene Families," Cell 52:925–933 (1988).

Staunton et al., "The Arrangement of the Immunoglobulin––Like Domains of ICAM–1 and the Binding Sites for LFA–1 and Rhinovirus," Cell 61:243–254 (1990).

Staunton et al., "A Cell Adhesion Molecule, ICAM–1, is the Major Surface Receptor for Rhinoviruses," Cell 56:849–853 (1989).

Sundquist et al., "Influenza Virus ISCOMs: Antibody Response in Animals", Vaccine 6:49–53 (1988).

Tomassini, J.E., "Isolation, Characterization and Cloning of the Cellular Receptor for the Major Group of Human Rhinoviruses," Ph.D. Thesis, University of Pennsylvania (1986).

Tomassini, J.E. and Colonno, R. J., "Isolation of a Receptor Protein Involved in Attachment of Human Rhinoviruses," J. Virol. 58(2):290–295 (1986).

Tomassini et al., "cDNA Cloning Reveals that the Major Group Rhinovirus Receptor on HeLa Cells is Intercellular Adhesion Molecule 1," PNAS 86:4907–4911 (1989).

Towbin et. al., "Electrophoretic Transfer of Proteins from Polyacrylamide Gels to Nitrocellulose Sheets: Procedure and Some Applications", PNAS 76(9):4350–4354 (1979).

Traunecker et al., "Highly Efficient Neutralization of HIV with Recombinant CD4–Immunoglobulin Molecules," Nature 339: 68–70 (1989).

Traunecker et al., "Soluble CD4 Molecules Neutralize Human Immunodeficiency Virus Type 1" Nature 331:84–86 (1988).

Turner et al., "Efficacy of Oral WIN 54954 for Prophylaxis of Experimental Rhinovirus Infection", 37:297–300 (1993).

Urlaub, G. and Chasin, L. A., "Isolation of Chinese Hamster Cell Mutants Deficient in Dihydrofolate Reductase Activity," PNAS USA 77(7):4216–4220 (1980).

Wade, N., "Hybridomas: A Potent New Biotechnology," Science 208:692–693 (1980).

Welsh, K.I., "Antibody Production Made Easier," Nature 266: 495 (1977).

Wigler et al., "Transformation of Mammalian Cells with Genes from Procaryotes and Eucaryotes," Cell 16:777–785 (1979).

Williams, A. F., "A Year in the Life of the Immunoglobulin Superfamily", Immunology Today 8(10):298–303 (1987).

Williams, A. F. and Barclay, A. N.,"The Immunoglobulin Superfamily–Domains for Cell Surface Recognition[1,2]", Ann. Rev. Immunol. 6:381–405 (1988).

Winther et al., "Sites of Rhinovirus Recovery After Point Inoculation of the Upper Airway", JAMA 256(13):1763–1767 (1986).

Woods et al., "In Vitro and In Vivo Activities of WIN 54954, a New Broad Spectrum Antipicornavirus Drug", Antimicrob. Agents Chemother 33:2069–2074 (1989).

Zettlmeissl et al., "Expression and Characterization of Human CD4: Immunoglobulin Fusion Proteins," DNA and Cell Biology 9: 347–353 (1990).

Braude, A. (ed.s), "Infectious Diseases and Medical Microbiology, 2nd edition, W.B. Saunders Co., Philadelphia, PA, (1986) chapter 65 Picornaviruses", pp. 521–529.

Gennaro, A.R. (ed.), Remington's Pharmaceutical Sciences, 18th edition, Mack Publishing Co., Easton, PA (1990), "Drug Absorption, Action and Disposition", pp. 707–721.

Martin et al., "Efficient Neutralization and Disruption of Rhinovirus by Chimeric ICAM–1/Immunoglobulin Molecules", J. Virology, 67(6):3561–3568 (Jun. 1993).

Hendley et al., "Transmission of Rhinovirus Colds By Self–Inoculation", The New England Journal of Medicine, 288(26):1361–1364 (Jun. 28, 1973).

Hendley, J. O., and Gwaltney, J. M., Jr., "Mechanisms of Transmission of Rhinovirus Infections", Epidemiologic Reviews, 10:242–257 (1988).

Suter, David, Associated Press, "Tests for a Nasal Spray to Deflect Cold Viruses", New York Times, Sep. 20, 1995.

Manning, Anita, "War on Bacteria Mix of Victories Amid Warnings", USA Today, Sep. 20, 1995.

Haney, Daniel Q., "Beyond Chicken Soup. Nasal Spray Keeps Chimps From Catching Cold Virus", St. Louis Post Dispatch, Sep. 20, 1995.

Associated Press, "Common Colds: Nasal Spray May Help Keep The Sniffles Away", Atlanta Constitution, Sep. 20, 1995.

Associated Press, "Drug Sprays Away Colds", New York Post, Sep. 20, 1995.

Haney, Daniel Q., Associated Press, "The Cold War: Scientists Develop Spray That May End Sniffles", Arizona Republic, Sep. 20, 1995.

Haney, Daniel Q., Associated Press, "For Colds, Nasal Spray Holds Hope. A Protein Swamps The Virus With Potential Targets In The Nose. Its a Decoy Trick", Philadelphia Inquirer, Sep. 20, 1995.

Associated Press, "Simple Nasal Spray May Be Able To Keep Common Cold Away. Medicine Successful On Chimps So Far", Washington Times, Sep. 20, 1995.

Associated Press, "Doctors Sniffing Out Spray to Fight Colds", Denver Post, Sep. 20, 1995.

Associated Press, "Someday Soon, A Simple Sniff Should Snuff The Sniffles", Houston Chronicle, Sep. 20, 1995.

Haney, Daniel Q., Associated Press, "Spray May Ward Off Sniffles. Nasal Treatment Studies To Keep Cold Viruses From Invading Victim", Denver–Rocky Mountain News, Sep. 20, 1995.

Haney, Daniel Q., Associated Press, "Scientists Make Headway In Cold War With Nose Spray", Chicago Sun–Times, Sep. 20, 1995.

Haney, Daniel Q., Associated Press, "Labs Busy Working On Nose Spray To Keep Colds Away", Charlotte Observer, Sep. 20, 1995.

Associated Press, "Nasal Spray May Prevent Sniffles", Miami Herald, Sep. 20, 1995.

Associated Press, "Cure For The Cold? No, But Prevention May Be Spray Away", San Diego Union–Tribune, Sep. 20, 1995.

Haney, Daniel Q., "Nasal Spray Touted As Next–Best Thing To Cure For Colds", The Montreal Gazette, Sep. 20, 1995.

Associated Press, "Scientists Feel They Can Develop Spray To Keep The Sniffles Away", The Spectator, Sep. 20, 1995.

Haney, Daniel Q., Associated Press, "New Nasal Spray May Take Sniffles Out Of Common Cold", Cleveland Plain Dealer, Sep. 20, 1995.

Associated Press, No Cure, But Nothing To Sniff(le) At. Nasal Spray To Block Common Cold Is In The Works, Minneapolis Star Tribune, Sep. 20, 1995.

Haney, Daniel Q., Associated Press, "Out Front: Progress On Cold Front. Spray May Ward Off Sniffles. Medicine Is First To Block Infection", Sep. 19, 1995.

Monitoring Report, "Cure For Colds Sep. 18 to Sep. 20", Video Monitoring Services of America, a Burrelle's Affiliate, New York, New York, pp. 1–3, Sep. 20, 1995.

Al–Nakib, W., P.G. Higgins, G.I. Barrow, D.A.J. Tyrrell, K. Andries, G. Vanden Bussche, N. Taylor, and P.A.J. Janssen, "Suppression of Colds in Human Volunteers Challenged with Rhinovirus by a New Synthetic Drug (R61837)", Antimicrobial Agents and Chemotherapy 33(4): 522–525 (Apr. 1989).

Amzel, L. M., and R.J. Poljak,"Three–Dimensional Structure of Immunoglobulins", Ann. Rev. Biochem. 48: 961–997 (1979).

Becker, J. W., and G.N.Reeke, Jr., "Three–dimensional structure of $\beta_2$–microglobulin", Proc. Natl. Acad. Sci. USA 82: 4225–4229 (Jun. 1985).

Becker, J. W., H.P. Erickson, S. Hoffman, B.A. Cunningham, and G.M. Edelman, "Topology of cell adhesion molecules", Proc. Natl. Acad. Sci. USA, 86: 1088–1092 (Feb. 1989).

Bjorkman, P. J., M.A. Saper, B. Samraoui, W.S. Bennett, J.L. Strominger, and D.C. Wiley, "Structure of the human class I histocompatibility antigen, HLA–A2", Nature 329: 506–512 (Oct. 1987).

Colman, P. M., "Structure of Antibody–Antigen Complexes: Implications for Immune Recognition", Advances in Immunology 43: 99–132 (1988).

Colonno, R. J., J.H. Condra, S. Mizutani, P.L. Callahan, M.–E.Davies, and M.A. Murcko, "Evidence for the direct involvement of the rhinovirus canyon in receptor binding", Proc. Natl. Acad. Sci. USA 85: 5449–5453 (Aug. 1988).

Craig, A. G. and A.R. Berendt, "The Role of ICAM–1 as a Receptor for Rhinovirus and Malaria", in *Integrins and ICAM–1 in Immune Responses*, N. Hodd, ed. (Chem Immunol. Basel, Karger, 1991), vol. 50, pp. 116–134 (1991).

Crump, C. E., E. Arruda, and F.G. Hayden, "Comparative Antirhinoviral Activities of Soluble Intercellular Adhesion Molecule–1(sICAM–1) and Chimeric ICAM–1/Immunoglobulin A Molecule", Antimicrobial Agents and Chemotheray 38(6): 1425–1427 (Jun. 1994).

Dayhoff, M. O., W.C. Barker, and L.T. Hunt, "Establishing Homologies in Protein Sequences", Methods in Enzymology 91: 524–545 (1983).

Dearden, C., W. Al–Nakib, K. Andries, R. Woestenborghs, and D.A.J. Tyrrell, "Drug resistant rhinoviruses from the nose of experimentally treated volunteers", Arch. Virol. 109: 71–81 (1989).

Dustin, M. L. and T.A. Springer, "Lymphocyte Function-–associated Antigen–1 (LFA–1) Interaction with Intercellular Adhesion Molecule–1 (ICAM–1) is One of At Least Three Mechanisms for Lymphocyte Adhesion to Cultured Endothelial Cells", J. Cell Biol. 107: 321–331 (Jul. 1988).

Ezekovitz, R.A.B., R.B. Sim, G.G. MacPherson, and S. Gordon, "Interaction of Human Monocytes, Macrophages, and Polymorphonuclear Leukocytes with Zymposan in Vitro: Role of Type 3 Compliment Receptors and Macrophage Derived Complement", J. Clin. Invest. 76: 2368–2376 (Dec. 1985).

Greve, J. M., C.P. Forte, C.W. Marlor, A.M. Meyer, H. Hoover–Litty, D. Wunderlich, and A. McClelland, "Mechanisms of Receptor–Mediated Rhinovirus Neutralization Defined by Two Soluble Forms of ICAM–1", J. Virol. 65(11): 6015–6023 (Nov. 1991).

Guttman, N., and D. Baltimore, "Plasma Membrane Component Able to Bind and Alter Virions of Poliovirus Type 1: Sutides on Cell–Free Alteration Using a Simplified Assay", Virol. 82: 25–36 (1977).

Gwaltney, J. M., Jr., and J.O. Hendley, "Rhinovirus Transmission: One if by Air, Two if by Hand", Trans. Am. Clin. Climatol, Assoc. 89: 194–200 (1977).

Gwaltney, J. M.,Jr., and J.O. Hendley, "Rhinovirus Transmission One if by Air, Two if by Hand", Am. J. Epid. 107(5): 357–361 (May 1978).

Gwaltney, J. M., Jr., "Rhinovirus colds: epdimiology, clinical characteristics and transmission", Eur. J. Respir. Dis. 64 (suppl. 128): 336–339 (1983).

Gwaltney, J. M., Jr., "Rhinoviruses", Yale J. Biol. Med. 48: 17–45 (1975).

Hayden, F. G., and J.M. Gwaltney, Jr., "Intranasal Interferon–$\beta_2$ Treatment of Experimental Rhinoviral Colds", J. Infect. Dis. 150(2): 174–180 (Aug. 1984).

Hendley, J. O., and J.M. Gwaltney, Jr., "Mechanisms of Transmission of Rhinovirus Infections", Epidemiologic Reviews 10: 242–258 (1988).

Horley, K. J., C. Carpenito, B. Baker, and F. Takei, "Molecular cloning of murine intercellular adhesion molecule (ICAM–1)", EMBO J. 8(10): 2889–2896 (1989).

Jacobs, K., C. Shoemaker, R. Rudersdorf, S.D. Neill, R.J. Kaufman, A Mufson, J. Seehra, S.S. Jones, R. Hewick, E.F. Fritsch, M. Kawakita, T. Shimizu, and T. Miyake, "Isolation and characterization of genomic and cDNA clones of human erythropoietin", Nature 313: 806–810 (Feb. 1985).

Kim S., T.J. Smith, M.S. Chapman, M.G. Rossmann, D.C. Pevear, F.J. Dutko, P.J. Felock, G.D. Diana, and M.A. McKinlay, "Crystal Structure of Human Rhinovirus Serotype 1A (HRV1A)", J. Med. Biol. 210: 91–111 (1989).

Layne S. P., M.J. Merges, M. Dembo, J.L. Spouge, and P.L. Nara, "HIV requires multiple gp120 molecules for CD4–mediated infection", Nature 346: 277–279 (Jul. 1990).

Leonard, W. J., J.M. Depper, G.R. Crabtree, S. Rudikoff, J. Pumphrey, R.J. Robb, M. Krünke, P.B. Svetlik, N.J. Peffer, T.A. Waldmann, and W.C. Greene, "Molecular cloning and expression of cDNAs for the human interleukin–2 receptor", Nature 311: 626–631 (Oct. 1984).

Leszczynski, J. F., and G.D. Rose, "Loops in Globular Proteins: A Novel Category of Secondary Structure", Science 234: 849–855 (Nov. 1986).

Lineberger, D. W., D.J. Graham, J.E. Tomassini, and R.J. Colonno, "Antibodies that Block Rhinovirus Attachment Map to Domain 1 of the Major Group Receptor", J. Virol. 64(6): 2582–2587 (Jun. 1990).

Martin, S., J.M. Casanovas, D.E. Staunton, and T.A. Springer, "Erfolgreiche Blockade von Rhinovirusinfektionen durch ICAM–1–Immunoglobulinchimare in vitro", Med. Klin. 88(4): 193–197 (1993).

McPherson, J. M., and D.J. Livingston, "Protein Engineering: New Approaches to Improved Therapeutic Proteins, Part I", in *Biotech. Trends*, S. Petska, ed. (Pharmaceutical Technology, May 1989).

Livingston, D. J., and J.M. McPherson, "Protein Engineering: New Approaches to Improved Therapeutic Proteins, Part II", in *Biotech. Trends*, S. Petska, ed. (Pharmaceutical Technlogy, Jun. 1989).

McPherson, J. M., and D.J. Livingston, "Protein Engineering: New Approaches to Improved Therapeutic Proteins, Part III", in *Biotech. Trands*, S. Petska, ed. (Pharmaceutical Technology, Sep. 1989).

McClelland, A., M.E.Kamarck, F.H. Ruddle, "Molecular Cloning of Receptor Genes by Transfection", Methods in Enzymology 147: 280–291 (1987).

Minor, P. D., "Chapter 2: Growth, Assay and Purification of Picornaviruses", in *Virology: a practical approach* (IRL Press, Washington, D.C., 1985), pp. 25–41.

Minor, P. D., P.A. Pipkin, D. Hockley, G.C. Schild, and J.W. Almond, "Monoclonal antibodies which block cellular receptors of poliovirus", Virus Res. 1: 203–212 (1984).

Morein B., "Potentiation of the Immune Response by Immunization with Antigens in Defined Multimeric Physical Forms", Vet. Immunol. Immunopathol. 17: 153–159 (1987).

Ockenhouse, C.F., R. Betageri, T.A. Springer, and D.E. Staunton, "Plasmodium falciparum–Infected Erythrocytes Bind ICAM–1 at a Site Distinct from LFA–1, Mac–1, and Human Rhinovirus", Cell 68: 63–69 (Jan. 1992).

Peppel, K., D. Crawford, and B. Beutler, "A Tumor Necrosis Factor (TNF) Receptor–IgG Heavy Chain Chimeric Protein as a Bivalent Antagonist of TNF Activity", J. Exp. Med. 174: 1483–1489 (Dec. 1991).

Pevear, D. C., M.J. Fancher, P.J. Felock, M.g. Rossmann, M.S. Miller, G. Diana, A.M. Treasurywala, M.A. McKinlay, and F.J. Dutko, "Conformational Change in the floor of the Human Rhinovirus Canyon Blocks Adsorption to HeLa Cell Receptors", J. Virol. 63(5): 2002–2007 (May 1989).

Plow, E. F., M.D. Pierschbacher, E. Ruoslahti, G.A. Marguerie, and M.H. Ginsberg, "The effect of Arg–Gly–Asp––containing peptides on fibrinogen and von Willebrand factor binding to platelets", Proc. Natl. Acad. Sci. USA 82: 8057–8061 (1985).

Ray, C.G., "Chapter 32: Respiratory Viruses", in *Medical Microbiology, an Introduction to Infectious Diseases*, 2nd Ed, J. C. Sherris, ed. (Elsevier, New York, 1990), pp. 499–516.

Roesing, T. G., P.A. Toselli, and R.L. Crowell, "Elution and Uncoating of Coxsackievirus B3 by Isolated HeLa Cell Plasma Membranes", J. Virol. 15(3): 654–667 (Mar. 1975).

Rossmann, M. G., "The Canyon Hypothesis. Hiding the Host Cell Receptor Attachment Site on a Viral Surface from Immune Surveillance", J. Biol. Chem. 264(25): 14587–14590 (Sep. 1989).

Saiki, R.K., D.H. Gelfand, S. Stoffel, S.J. Scharf, R. Higuchi, G.T. Horn, K.B. Mullis, and H.A. Erlich, "Primer–Directed Enzymatic Amplification of DNA with a Thermostable DNA Polymerase", Science 239: 487–491 (Jan. 1988).

Sayre, P.H., R.E. Hussey, H.–C. Chang, T.L. Ciardelli, and E.L. Reinherz, "Structural and Binding Analysis of a Two Domain Extracellular CD2 Molecule", J. Exp. Med. 169: 995–1009 (Mar. 1989).

Siu, G., S.M. Hedrick, and A.A. Brian, "Isolation of the Murine Intercellular Adhesion Molecule 1 (ICAM–1) Gene", J. Immun. 143(11): 3813–3820 (Dec. 1989).

Skern, T., W. Sommergruber, D. Blass, P. Gruendler, F. Fraundorfer, C. Pieler, I. Fogy, and E. Kuechler, "Human rhinovirus 2: complete nucleotide sequence and proteolytic processing signals in the capsid protein region", Nucleic Acids Research 13(6): 2111–2126 (1985).

Smilek, D. E., D.C. Wraith, S. Hodgkinson, S. Swivedy, L. Steinman, and H.O. McDevitt, "A single amino acid change in a myelelin basic protein peptide confers the capacity to prevent rather than induce experimental autoimmune encephalomyelitis", Proc. Natl. Acad. Sci. USA 88:9633–9637 (Nov. 1991).

Staunton, D.E., M.L. Dustin, and T.A. Springer, "Functional cloning of ICAM–2, a cell adhesion ligand for LFA–1 homologous to ICAM–1", Nature 339: 61–64 (May 1989).

Staunton, D.E., C.F. Ockenhouse, and T.A. Springer, "Soluble Intercellular Adhesion Molecule 1–Immunoglubulin G1 Immunoadhesin Mediates Phagocytosis of Malaria–infected Erythrocytes", J. Exp. Med. 176: 1471–1476 (Nov. 1992).

Uncapher, C. R., C.M. DeWitt, and R.J. Colonno, "The Major and Minor Group Receptor Families Contain All but One Human Rhinovirus Serotype", Virology 180: 814–817 (1991).

Wickner W. T., and H.F. Lodish, "Multiple Mechanisms of Protein Insertion Into and Across Membranes", Science 230: 400–407 (Oct. 1985).

Weis, W., J.H. Brown, S. Cusack, J.C. Paulson, J.J. Skehel, and D.C. Wiley, "Structure of the influenza virus haemagglutinin complexed with its receptor, sialic acid", Nature 333: 426–431 (Jun. 1988).

R&D Systems (Minneapolis, MN), 1994 Catalog, Item #BBE 1B, "Human Soluble ICAM–1".

"Chapter 9, Introduction of DNA into Mammalian Cells", Current Protocols in Molecular Biology 1997: 9.0.1–9.9.16 (1997).

British Biotechnology, Ltd. (Oxford, England), 1993 Product Catalog, Item #BBE 1, "Soluble ICAM–1 ELISA".

Steis, R.G., L. Marcon, J. Clark, W. Urba, D.L. Longo, D.L. Nelson, and A.E. Maluish, "Serum soluble IL–2 receptor as a tumor marker in patients with hairy cell leukemia", Blood (May 1988) 7195:1304–9.

Harning, R., E. Mainolfi, J.C. Bystryn, M. Henn, V.J. Merluzzi, and R. Rothlein, "Serum levels of circulating intercellular adhesion molecule 1 in human malignant melanoma", Cancer Res. (1991) 51(8):5003–5.

Shipkowitz, N.L., R.R. Bower, J.B. Schleicher, F. Aquino, R.N. Appell, and W.R. Broderick, "Antiviral Activity of a bis–Benzimidazole Against Experimental Rhinovirus Infections in Chimpanzees", App. Microbiol. (1972) 23(1):117–122.

Sundquist, B., K. Lövgren, S. Höglund, and B. Morein, "Influenza virus ISCOMs: biochemical characterization", Vaccine (Feb. 1988) 6:44–48.

Bella, J., P.R. Kolatkar, C.W. Marlow, J.M. Greve, and M.G. Rossmann, "The structure of the two amino–terminal domains of human ICAM–1 suggests how it functions as a rhinovirus receptor and as an LFA–1 integrin ligand", P.N.A.S. USA 95:4140–4145 (Apr. 1998).

Bella, J., P.R. Kolatkar, C.W. Marlor, J.M. Greve and M.G. Rossmann, "The structure of the two amino–terminal domains of human intercellular adhesion molecule–1 suggests how it functions as a rhinovirus receptor", Virus Res. 62:107–117 (1999).

Casanovas, J.M., J.K., Bickford, and T.A. Springer, "The Domain Structure of ICAM–1 and the Kinetics of Binding to Rhinovirus", J. Virol. 72(7): 6244–6246 (Jul. 1998).

Casanovas, J.M., and T.A. Springer, "Pathway of Rhinovirus Disruption to Soluble Intercellular Adhesion Molecule 1 (ICAM–1):An Intermediate in Which ICAM–1 is Bound and RNA is Released", J. Virol. 68(9):5882–9 (Sep. 1994).

Casanovas, J.M., and T.A. Springer, "Kinetics and Thermodynamics of Virus Binding to Receptor. Studies with Rhinovirus, Intercellular Adhesion Molecule–1 (ICAM–1), and Surface Plasmon Resonance", J. Biomed. Chem. 270(22):13216–13224 (Jun. 1996).

Casasnovas, J.M., T. Stehle, J.-H. Liu, J.-H Wang, and T.A. Springer, "A dimeric crystal structure for the N-terminal two domains of intercellular adhesion molecule–1", Proc. Natl. Acad. Sci. USA 95:4134–4139 (Apr. 1998).

Greve, J.M. and M.G. Rossmann, "12. Interaction of Rhinovirus with Its Receptor, ICAM–1", in *Cellular Receptor of Animal Viruses* [Cold Spring Harbor Laboratory Press, 1994], pp. 195–213.

Huguenel, E.D., D. Cohn, D.P. Dockum, J.M. Greve, M.A. Fournel, L. Hammond, R. Irwin, J. Mahoney, A. McClelland, E. Muchmore, A.C. Ohlin, and P. Scuderi, "Prevention of Rhinovirus Infection in Chimpanzees by Soluble Intercellular Adhesion Molecule–1", Am. J. Respir. Crit. Care Med. 155:1206–1210 (1997).

Kolatkar, P.R., M.A. Oliveira, M.G. Rossmann, A.H. Robbins, S.K. Katti, H. Hoover-Litty, C. Forte, J.M. Greve, A. McClelland, and N.H. Olson, "Preliminary X–Ray Crystallographic Analysis of Intercellular Adhesi n Molecule–1", J. Mol. Biol. 225:1127–1130 (1992).

Olson, N.H., P.R. Kolatkar, M. A. Olveira, R. H. Cheng, J.M. Greve, A. McClelland, T.S. Baker, and M.G. Rossmann, "Structure of a human rhinovirus complexed with its receptor molecule", Proc. Natl. Acad. Sci. USA 90:507–511 (Jan. 1993).

Rossmann, M.G., N.H. Olson, P.R. Kolatkar, M.A. Oliveira, R.H. Cheng, J.M. Greve, A. McClelland, and T.S. Baker, "Crystallographic and cryo EM analysis of virion–receptor interactions", Arch. Virol. [Suppl] 9:531–541 (1994).

The Journal of Immunology, vol. 137, No. 4, Aug. 15, 1986, pp. 1270–1274, The American Association of Immunologists, R. Rothlein et al.; A Human Intercellular adhesion molecule (ICAM–1) distinct from LFA–1.

Nature, vol. 331 Feb. 18, 1988, pp. 624–627, D. Simmons et al; ICAM, an adhesion ligand of LFA–1, is homologous to the neural cell adhesion molecule NCAM.

Journal of Virology, vol. 58, No. 2, May 1986, pp. 290–295, J.E. Tomassini et al; Isolation of a receptor protein involved in attachment of human rhinoviruses.

Cell, vol. 52, Mar. 25, 1988, pp. 925–933, Cell Press, D.E. Straunton et al; Primary Structure of ICAM–1 demonstrates interaction between members of the immunoglobulin and intyegrin supergene families.

Cell vol. 51, Dec. 4, 1987, pp. 813–819, Cell Press, S.D. Marlin et al; Purified intercellular adhesion molecule–1 (ICAM–1) is a ligand for lymphocyte function–associated antigen 1 (LFA–1).

Bowie, J. U., et al., Science 247:1306–1310 (1990), "Deciphering the message in protein sequences: tolerance to amino acid substitutions".

Gething, J–J., et al. Nature 300:498–603 (1982), "Construction of influenza haemagglutinin genes that code for intracellular and secreted forms of the protein".

Marguiles, D. H., et al., Immunol. Res. 6:101–116 (1987), "Engineering soluble major histocompatibility molecules: why and how".

Ruoslahti, E., et al., in *Synthetic peptides in biology and medicine*, edited by K. Alitalo, et al., Elsevier Science Publishers, New York (1985), pp. 191–197, "Synthetic peptides in the analysis of cell adhesion".

Staunton, D. E., et al., Cell 56:849–853 (1989), "A cell adhesion molecule, ICAM–1, is the major surface receptor for rhinoviruses".

Staunton, D. E., et al., Cell 52:925–933 (Mar. 25, 1988), "Primary structure of ICAM–1 demonstrates interaction between members of the immunoglobulin and integrin supergene families".

Tomassini, J. E., et al., J. Virology 58(2):290–295 (May 1986), "Isolation of a receptor protein involved in attachment of human rhinoviruses".

* cited by examiner

Intercellular adhesion molecule-1(ICAM-1)

```
           1
Asn Ala Gln Thr Ser Val Ser Pro Ser Lys
                                     . . .

10
Val Ile Leu Pro Arg Gly Gly Ser Val Leu
 |   . . . . -----94---->

20
Val Thr Cys Ser Thr Ser Cys Asp Gln Pro

30
Lys Leu Leu Gly Ile Glu Thr Pro Leu Pro

40
Lys Lys Glu Leu Leu Leu Pro Gly Asn Asn
     . . . |  . . . ---- 94&96 ---------------

50
Arg Lys Val Tyr Glu Leu Ser Asn Val Gln
-->|  . . . ------ (25k)--91&115&142&147---

60
Glu Asp Ser Gln Pro Met Cys Tyr Ser Asn
------------------------      ----. . . ,----

70
Cys Pro Asp Gly Gln Ser Thr Ala Lys Thr
 ---     . . . ---                 . . . >

80
Phe Leu Thr Val Tyr Trp Thr Pro Glu Arg
```

FIG. 1A

```
                    90
        Val Glu Leu Ala Pro Leu Pro Ser Trp Gln

100
        Pro Val Gly Lys Asn Leu Thr Leu Arg Cys

110
        Gln Val Glu Gly Gly Ala Pro Arg Ala Asn

120
        Leu Thr Val Val Leu Leu Arg Gly Glu Lys
                                             ...

130
        Glu Leu Lys Arg Glu Pro Ala Val Gly Glu
         |  ------ (34k) --103&114&121&135 ----

140
        Pro Ala Glu Val Thr Thr Thr Val Leu Val
        ---------------------- (xx) ------------

150
        Arg Arg Asp His His Gly Ala Asn Phe Ser
         ..........   ............       ...>

160
        Cys Arg Thr Glu Leu Asp Leu Arg Pro Gln

170
        Gly Leu Glu Leu Phe Glu Asn Thr Ser Ala
```

FIG. 1B

```
            180
Pro Tyr Gln Leu Gln Thr Phe Val Leu Pro

190
Ala Thr Pro Pro Gln Leu Val Ser Pro Arg
                                     . . .

200
Val Leu Glu Val Asp Thr Gln Gly Thr Val
 | (x) ------- (50k) -- 110 -------------

210
Val Cys Ser Leu Asp Gly Leu Phe Pro Val
 ----      ------    ------------------

220
Ser Glu Ala Gln Val His Leu Ala Leu Gly
 .... -------        ---      ....  ...>

230
Asp Gln Arg Leu Asn Pro Thr Val Thr Tyr

240
Gly Asn Asp Ser Phe Ser Ala Lys Ala Ser

250
Val Ser Val Thr Ala Glu Asp Glu Gly Thr

260
Gln Arg Leu Thr Cys Ala Val Ile Leu Gly
```

FIG. 1C

```
            270
Asn Gln Ser Gln Glu Thr Leu Gln Thr Val

280
Thr Ile Tyr Ser Phe Pro Ala Pro Asn Val

290
Ile Leu Thr Lys Pro Glu Val Ser Glu Gly

300
Thr Glu Val Thr Val Lys Cys Glu Ala His

310
Pro Arg Ala Lys Val Thr Leu Asn Gly Val

320
Pro Ala Gln Pro Leu Gly Pro Arg Ala Gln

330
Leu Leu Leu Lys Ala Thr Pro Glu Asp Asn

340
Gly Arg Ser Phe Ser Cys Ser Ala Thr Leu

350
Glu Val Ala Gly Gln Leu Ile His Lys Asn
```

FIG. 1D

```
       360
Gln Thr Arg Glu Leu Arg Val Leu Tyr Gly

370
Pro Arg Leu Asp Glu Arg Asp Cys Pro Gly

380
Asn Trp Thr Trp Pro Glu Asn Ser Gln Gln

390
Thr Pro Met Cys Gln Ala Trp Gly Asn Pro

400
Leu Pro Glu Leu Lys Cys Leu Lys Asp Gly
                              ····|······

410
Thr Phe Pro Leu Pro Ile Gly Glu Ser Val
····------97&46------------------------

420           425
Thr Val Thr Arg Asp Leu Glu Gly Thr Tyr
---------------------------------   ---

430
Leu Cys Arg Ala Arg Ser Thr Gln Gly Glu
----(xx)------------···>

440
Val Thr Arg Glu Val Thr Val Asn Val Leu
```

FIG. 1E

```
       450
Ser Pro Arg Tyr Glu Ile Val Ile Ile Thr

460
Val Val Ala Ala Ala Val Ile Met Gly Thr

470
Ala Gly Leu Ser Thr Tyr Leu Tyr Asn Arg

480
Gln Arg Lys Ile Lys Lys Tyr Arg Leu Gln
                         ····|··· -----96---
                       ····|············-----94---

490
Gln Ala Gln Lys Gly Thr Pro Met Lys Pro
---------------->|···· ---91&142------
-------------···>

500             505
Asn Thr Gln Ala Thr Pro Pro
---------------->
```

FIG. 1F

ANTIVIRAL METHODS USING HUMAN RHINOVIRUS RECEPTOR (ICAM-1)

This is a continuation of application U.S. Ser. No. 08/066,404 filed May 21, 1993, now abandoned, which is a continuation of U.S. Ser. No. 07/678,909 filed Mar. 28, 1991, abandoned, which is a continuation of U.S. Ser. No. 07/390,662 filed Aug. 10, 1989, abandoned, which is a continuation-impart of U.S. Ser. No. 07/239,571 filed Sep. 1, 1988 abandoned, and a continuation-in-part of U.S. Ser. No. 07/262,428 filed Oct. 25, 1988, abandoned, which is a continuation-in-part of U.S. Ser. No. 07/239,571, abandoned.

BACKGROUND OF THE INVENTION

The present invention relates to the isolation of proteins from animal cells, particularly mammalian cells, that bind to human rhinovirus (HRV). More particularly, the invention relates to the isolation of HRV receptor proteins that can bind to HRV and thereby block the infectivity of the virus. This property can serve as a basis for inhibiting the initiation or the spread of HRV infections, better known as the common cold.

In order to infect host cells, viruses must bind to and then enter cells to initiate an infection. Since 1959, evidence has accumulated in the literature indicating that the presence of specific binding sites (receptors) on host cells could be a major determinant of tissue tropism of certain viruses. [Holland, J. J., and McLaren, L. C., The mammalian cell-virus relationship. II. Absorption, reception, and eclipse of the poliovirus by HeLa cells, J. Exp. Med. 109, 487–504 (1959). Holland, J. J., Receptor affinities as major determinants of enterovirus tissue tropisms in humans, Virology 15, 312–326 (1961).] Among picornaviruses such as poliovirus, coxsackie virus, and rhinoviruses, specific binding to host cells has been demonstrated. By competition experiments, it has been demonstrated that some of these receptors are distinct from one another in that the saturation of the receptor of one virus had no effect on the binding of a second virus. [Lonberg-Holm, K, Crowell, R. L., and Philipson, L. Unrelated animal viruses share receptors, Nature 259, 679–681 (1976)].

Rhinoviruses form the largest family of picornaviruses, with 115 distinct serotypes identified to date. A large fraction of rhinoviruses (estimated to be 80%) appear to bind to a common receptor on human cells. [Abraham, G., and Colonno, R. J., Many rhinovirus serotypes share the same cellular receptor, J. of Virology 51, 340–345 (1984).] In 1985, the isolation of a monoclonal antibody that appeared to be directed against the major rhinovirus receptor was described. [Colonno, R. J., Callahan, P. L., and Long, W. J., Isolation of a monoclonal antibody that blocks attachment of the major group of human rhinoviruses, J. of Virology 57, 7–12 (1986).] It inhibited infection of cells with the appropriate serotypes of rhinovirus and it inhibited binding of radiolabeled rhinovirus to cells. This group subsequently reported that the monoclonal antibody bound to a protein with an apparent molecular weight of 90,000 daltons. Tomassini, J. E., and Colonno, R. J., Isolation of a receptor protein involved in attachment of human rhinoviruses, J. of Virology 58, 290–295 (1986).) This monoclonal antibody has been utilized in clinical trials with primates and humans and is understood to provide some protection against rhinovirus infection.

There are several other reports of attempts at therapeutic intervention in rhinovirus infections. Intranasal application of interferon in humans has been attempted. [Douglas, R. M., et al., Prophylactic efficacy of intranasal alpha2-interferon against rhinovirus infections in the family setting, The New England J. of Medicine, 314, 65–75 (1986).] In this case, significant reduction in the severity of the infection was found, although nosebleeds were observed as a side-effect. Also, several analogs of disoxaril ("WIN" compounds) that reduce the infectivity of a number of picornaviruses (with widely varying effectiveness, depending on the serotype) have been tested in tissue culture and in some animal models.. [Fox, M. P., Otto, M. J., and McKinlay, M. A., Antimicrob. Ag. and Chemotherapy 30, 110–116 (1986).] These compounds appear to inhibit replication at a step subsequent to receptor binding, probably at some step of virus uncoating. The atomic coordinates of the binding sites of these compounds within the viral capsid of the serotype HRV14 have been determined by x-ray crystallography, and are located in a hydrophobic pocket present in each protomeric unit of the capsid. [Smith, T. J., et al., The site of attachment in human rhinovirus 14 for antiviral agents that inhibit uncoating, Science 233, 1286–1293 (1986).] The specific function of the binding pocket, if any, is unknown, but drug-resistant mutants with single amino acid interchanges in this region arise at high frequency and are viable. [Badger, J. et al., Structural analysis of a series of antiviral agents complexed with human rhinovirus 14, PNAS 85, 3304–3308 (1988).] This result calls into question the efficacy of such compounds as drugs. The production of anti-peptide antibodies in rabbits has been reported using peptides derived from amino acid sequence of the viral capsid proteins t line the "receptor canyon" of HRV14. [McCray, J., and Werner, G., Different rhinovirus serotypes neutralized by antipeptide antibodies, Nature 329:736–738 (1987).] While the titers of these sera are quite low, cross-serotype protection of cells in tissue culture from rhinovirus infection was demonstrated, raising the possibility of a vaccine.

It is an object of the present invention to isolate an HRV receptor protein from cells having the property of blocking HRV infection. Given the high affinity the virus has for its receptor, it was hypothesized that a therapeutic agent effective against HRV infection might be the receptor itself, or more specifically, the virus binding domain of the receptor. A protein, protein fragment, or peptide that comprises the virus binding domain could block the ability of virus to bind to host cells by occupying (blocking) the receptor binding cleft on the virus. Furthermore, since such a molecule would make some or all of the molecular contacts with the virus capsid that the receptor does, virus mutations that adversely affect binding of the molecule would adversely affect binding of the receptor, and would thus be deleterious or lethal for the virus; therefore, the likelihood of drug-resistant mutants would be very low. Furthermore, such a molecule would be human, lowering the likelihood of being antigenic in humans.

SUMMARY OF THE INVENTION

It has been found that the human rhinovirus (HRV) major receptor can be isolated as a water soluble preparation which exhibits the desired property of binding to HRV capsids and substantially reducing infectivity of the virus. The preparation is in the form of detergent-complexed glycoprotein isolated from animal cells, preferably mammalian cells, that express the HRV major receptor. The purified receptor protein is characterized as follows. It is a glycoprotein with an apparent molecular weight of 95,000 daltons and includes the binding site for HRV. The glycoprotein contains 6–7 asparagine-linked oligosaccharide chains and exists in the preparation in the form of a detergent micelle-bound protein.

BRIEF DESCRIPTION OF THE DRAWINGS

FIG. 1. Amino acid sequence of ICAM-1 (minus signal sequence) [SEQ ID NO:1]. Sequences obtained from peptide fragments of HRR are indicated as dotted or dashed lines under corresponding sequence of ICAM; dashed means confidently assigned peptide sequences, dotted means ambiguous assignments, and "xx" means incorrect determinations of ambiguous assignments. The numbers under peptide sequences indicate code name of protein sequencing experiment.

DESCRIPTION OF THE PREFERRED EMBODIMENTS

Figure 2:
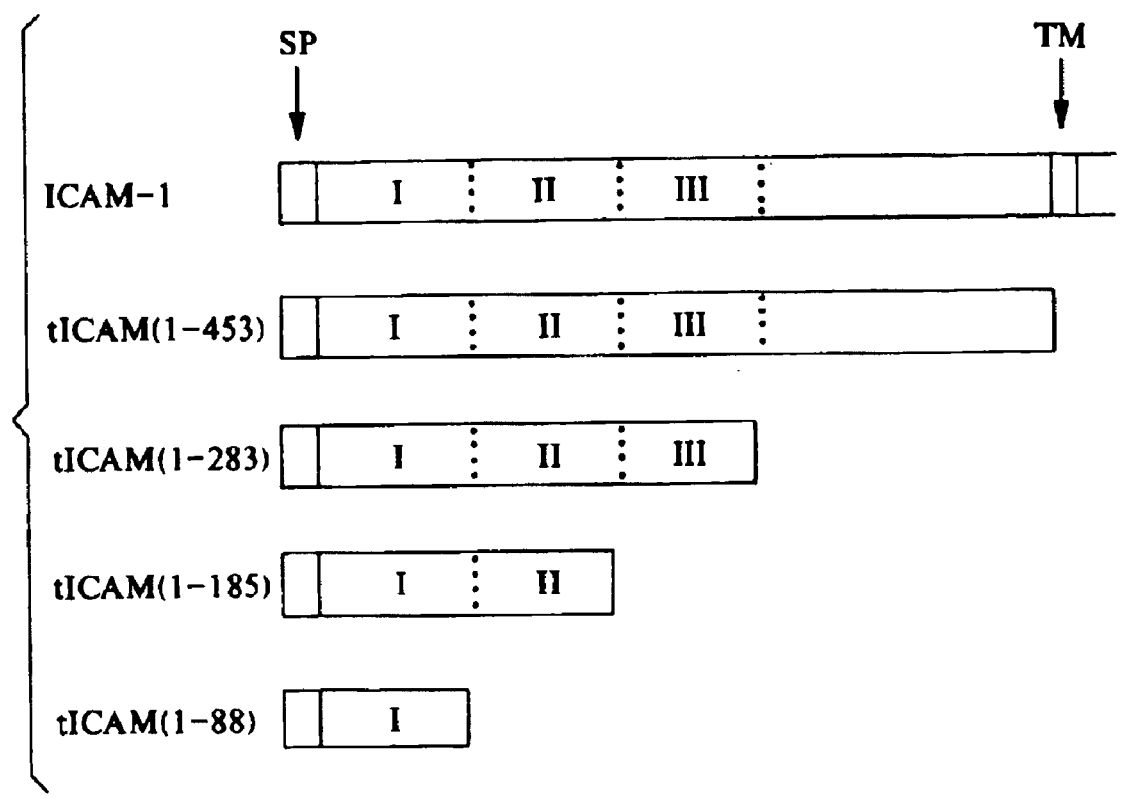
FIG. 2: Diagram of ICAM-1 domains numbered according to Staunton et al.

In general terms, the HRV major receptor preparation of the present invention can be obtained by extraction of appropriate animal cells that are known to express the HRV major receptor with a nonionic detergent, followed by immunopurification. Many human cell lines express the receptor, such as HeLa and WI38. Any of these human sources of HRV receptor can be extracted. Particularly useful are HeLa cells. Furthermore, non-human mammalian transfectant cell lines that express the HRV receptor are known or can be prepared which provide another useful source of the receptor. In particular, transfectant cell lines as described in Copending U.S. patent application Ser. No. 130,378, infra, provide a ready source of receptor, particularly those secondary transfectants that have been selected for overexpression of receptor. Other animal cells as are known in the art or developed hereafter, such as insect tissue culture cells that have been tranfected with the gene and express the receptor, can also be used.

Essentially any nonionic detergent can be used for the extraction provided the native conformation of the protein receptor is not destroyed. Denaturation of the receptor can be determined by monitoring the ability of the extracted protein to inhibit virus infectivity or by sensitivity to proteolysis. It has been determined that the receptor can be denatured by heating at 60° C. for 30 minutes or by treatment with 1% SDS indicating that care need be taken to maintain the native conformation of the HRV binding site. Examples of useful non-ionic detergents are the alkyl polyoxyethylene ethers (such as Brij), alkylphenyl polyoxyethelene ethers (such as Triton X-100 and Nonidet P-40), acyl polyoxyethylene sorbitan esters (such as Tween), and beta-D-alkyl glucosides, with Triton X-100 being considered particularly preferred.

The key step in the purification of the receptor is fractionation with highly selective anti-receptor antibody. The most ready means to obtain such an antibody is by monoclonal techniques. It is particularly preferred to produce mouse monoclonal antibodies by generating hybridoma cell lines from fusion of murine myeloma cells, and mouse transfectant cells expressing the HRV receptor. Further details are available in copending U.S. patent application Ser. No. 130,378, infra. After binding the detergent-glycoprotein complexes obtained from the cell extract to the selected monoclonal antibody, complexes bound to antibody are separated from the remainder of the mixture. Thereafter, detergent-receptor complexes bound to antibody are dissociated, taking steps to again prevent denaturation, and the resulting water soluble receptor preparation isolated.

Appropriate conditions for dissociating detergent-receptor complexes from the antibody can be determined empirically and can be expected to vary somewhat from antibody to antibody. Dissociation by raising pH has been found in some cases to be most effective with low pH or high salt conditions being operable but producing lower protein yields.

It is preferable to perform an intermediary purification before purification with antibody. Such intermediary steps comprise adsorbing the detergent extracted protein complexes to a lectin capable of binding HRV receptor, separating absorbed complexes from the remainder of the mixture, and dissociating such complexes for subsequent treatment with antibody. The selection of lectin and dissociating conditions is usually empirical. It has been found that the HRV receptor binds suitably to wheat germ agglutinin lectin and is dissociated effectively by washing with a solution of N-acetyl glucosamine. Because the oligosaccharides on the receptor protein are not completely characterized, and because the receptor protein can be glycosylated differently on different cell types (e.g., mouse cell transfectants), other lectins would be expected also to be suitable. The selection of an appropriate alternative to wheat germ agglutinin and/or eluting agent can be left to the ordinary skill in the art.

The resulting preparation can be treated with proteolytic agents such as proteases, e.g., trypsin, to produce smaller glycoprotein fragments that retain the ability to bind and reduce infectivity of HRV. For example, peptide fragments can be cleaved from a terminal region of the glycoprotein, e.g., the C-terminus, to yield glycoprotein fragments that retain HRV binding. Such glycoprotein fragments can, for example, have apparent molecular weights of between about 80,000 daltons and about 95,000 daltons. Smaller fragments which retain the HRV binding domain of the receptor are also considered to be within the scope of the present invention.

The receptor preparation of the present invention has been shown to inhibit the infectivity of the virus, presumably by binding to the HRV capsid to block its ability then to bind and infect human cells. Such an observation indicates that the receptor preparation will be useful in reducing the infection of host human cells in vivo by contacting the virus with the preparation under conditions favorable to binding with the virus. A therapeutic form would be that of an aqueous solution of the receptor in the presence of nonionic detergent to maintain the receptor in solution and in its native conformation. Detergents with lower critical micelle concentrations, such as the alkyl polyoxyethylene ether Brij 58, would be preferred in order to reduce the concentration of the detergent in the therapeutic solution. The receptor preparation can be administered in vivo by appropriate contact with those areas of the body susceptible to infection by HRV, e.g., by intranasal spray.

The present invention will now be illustrated, but is not intended to be limited, by the following examples.

Preparation of Purified Human Rhinovirus Receptor (HRR) Protein (1) Human cells (for example, Hela) or mouse L-cell transfectants (for example, the cell lines described in U.S. patent application Ser. No. 130,378, filed Dec. 8, 1987, McClelland and Meyer, "Transfectant Cell Lines Which Express the Major Human Rhinovirus Receptor") were grown up in large numbers as cellular monolayers in standard tissue culture medium (Dulbecco's modified essential medium containing 10% fetal bovine serum; transfectant cells were maintained in the same medium containing HAT (hypoxanthanine/aminopterin/thymidine) to maintain selective pressure for the selectable marker (Herpes TK). Cells were solubilized for 1 hour at 4° C. in a physiological buffer (Phosphate-buffered saline) containing a nonionic detergent (for example, Triton X-100) (T buffer) and a cocktail of protease inhibitors (aprotinin, leupeptin at 10 µg/ml, EDTA at 1 mM) to prevent proteolytic degradation of the receptor. Insoluble material was removed by filtration through a 0.22 µ filter.

(2) The extract was absorbed onto an affinity resin containing Wheat Germ Agglutinin (WGA) (Sigma Chemical Co., St. Louis, Mo., USA) crosslinked to Sepharose for 18 hours at 4° C. with gentle mixing (2 ml packed resin, containing 5 mg WGA/ml resin, per $10^9$ cells). The affinity resin was then washed extensively with buffer to remove unbound glycoproteins and eluted with the competing monosaccharide N-acetyl glucosamine (0.3M N-acetyl glucosamine in T buffer) for 1 hour at room temperature.

(3) The WGA-Sepharose eluant is then absorbed to an affinity resin to which purified monoclonal antibody to the HRR has been coupled (e.g., ATCC HB 9594, deposited on 19 Nov. 1987 with the American Type Culture Collection, 10801 University Boulevard, Manassas, Va. 20110-2209, referred to in the McClelland and Meyer patent application, Ser. No. 130,378, supra). The monoclonal antibody IgG was purified by ammonium sulfate precipitation [Parham, P., Meth. Enzymol. 92:110–138 (1983)], followed by affinity chromatography on either protein A Sepharose [Ey, P. L., et al., Immunochem. 15:429-436 (1978)] or an Abx column [J. T. Baker Co., Phillipsburg, N.J., USA] following the procedure described by the manufacturer. Monoclonal IgG affinity resin is prepared by coupling IgG to cyanogen bromide-activated Sepharose [Parham, P., supra.]

After adding 10 µg/ml human transferrin to block adsorption of transferrin receptor to the resin, the eluant is incubated at 4° C. for 18 hours with the resin with mixing (40–200 µl of resin, containing 5 mg IgG/ml resin, per $10^9$ cells), washed extensively with T buffer to remove unbound proteins, and then eluted under nondenaturing conditions with a high pH buffer (0.05 M diethanolamine (pH 11.5) with 0.1% Triton X-100) for 1 hour at room temperature. The eluant is removed, neutralized by the addition of 0.2 volumes of 1 M HEPES (pH 7.2), and dialysed against three changes of a physiological buffer containing a small amount of nonionic detergent to maintain the solubility of the receptor (0.01 M HEPES, 0.150 M NaCl, 0.001 M $CaCl_2$, 0.1% Triton X-100, pH 7.5).

The receptor may be further purified by velocity sedimentation through sucrose gradients to remove a group of minor high molecular weight (>200,000 daltons) contaminants. The receptor preparation is layered on top of a 15–35% sucrose gradient (total volume about 4.5 ml, and centrifuged at 300,000 X g for 18 hours at 4° C. Fractions are collected from the gradient and fractions containing the rhinovirus receptor, which sediments about ⅓ of the way down the gradient, are pooled, concentrated (if necessary), and dialysed.

(4) The resultant preparation from Hela cells was found to contain a glycoprotein with an apparent molecular weight of 95,000 daltons. From mouse transfectant cells, a protein of the same molecular weight but of greater heterogenity (upon analysis by SDS-PAGE) was isolated. The isolated protein has been shown to comprise the rhinovirus receptor by:

(a) Immunoprecipitation from $^{125}$I-surface labeled Hela cells and mouse transfectants expressing the human rhinovirus receptor with a monoclonal antibody that inhibits rhinovirus binding to cells.

(b) Immunoprecitation of purified, $^{125}$I-labeled receptor with the ATCC HB 9594 monoclonal antibody.

(5) A tryptic fragment was prepared by digesting the receptor with 1% (wt E/wt receptor protein) trypsin for 1 hour at 37° C. The reaction mixture was applied to a GF-450 gel filtration column (Dupont) equilibrated in N buffer and the proteolytic fragment separated from the enzyme. Analysis of the resultant fragments by SDS-PAGE indicated a mixture of a 90,000 dalton and an 83,000 dalton fragment of the receptor. These fragments eluted in the same position on a gel filtration column as intact receptor, suggesting that it is bound to a detergent micelle. Amino acid sequencing of the fragments yielded no sequence, indicating that they, like the intact receptor, have a blocked N-terminus, and further indicating that peptides lost from the 90,000 and 83,000 dalton fragments are from the C-terminus of the protein.

Characterization of the Preparation (1) The purity of the receptor preparation was assessed by SDS-PAGE followed by silver staining. Quantitation of protein was determined by comparing silver stained protein with a series of standard proteins of known amount on SDS-PAGE and confirmed by amino acid analysis, assuming a protein molecular weight of 50,000 daltons (determined by determining the apparent molecular weight on SDS-PAGE of deglycosylated receptor).

(2) The protein was shown to be a glycoprotein containing 6–7 asparagine-linked oligosaccharide chains by digestion of core-glycosylated receptor with endoglycosidase H. Upon gel filtration, the receptor eluted with a volume consistent with a protein molecular weight of 250,000 daltons. This data, along with evidence from chemical cross-linking experiments indicating the receptor is a monomer, are consistent with the receptor behaving like a protein bound to a detergent micelle.

(3) The purified receptor protein was shown to bind to rhinovirus in vitro. When incubated for 30 minutes at 34° C. with 1 µg/ml HRV14 or HRV3, unlabeled, $^{125}$I-labeled, and $^{35}$S-cysteine metabolically labeled HRR could be shown to associate with virus by sedimentation in sucrose gradients or by pelleting in a high speed centrifuge. This binding could be shown to be specific by competing the binding of radiolabeled receptor with unlabeled receptor. The in vitro reaction had the same temperature-dependency as in vivo: receptor bound to the virus at 37° C. but not at 4° C.

(4) The receptor was shown to inhibit infectivity of rhinovirus by incubating HRR with virus (under the same conditions as described above in which binding could be demonstrated) and then testing the resultant mixtures for infectivity by a standard limiting dilution infectivity assay. A Hela cell suspension was prepared by detaching with 0.03% EDTA/PBS for 10 minutes, and the cells washed in 2% FBS/DMEM (I medium) with 10 mM HEPES and adjusted to a concentration of $1.1 \times 10^7$ cells/ml. Virus or virus-receptor mixtures were serially diluted in I medium, and 20 µl of virus was mixed with 180 µl of cells and incubated for 60 minutes at room temperature. The mixture was then diluted with 9 volumes of I medium and plated out into 8–10 wells of a 96 well tissue culture plate (approximately 200 µl/well), and cultured at 34° C. for 5 days. Cultures were then scored by CPE (cytopathic effect) and the titer of the original stock determined by the following formula:

dead wells/10×50X dilution factor=PFU/ml

The results are shown in the Table below.

| Bit Number | |
|---|---|
| 20 | 1 |
| 010xxxxxxxxxxxxxxxxx | |
| 011xxxxxxxxxxxxxxxxx | |
| 1000000000000000000x | |

Additional HRV serotypes were tested. HRV 4, 11, 17 and 89 serotypes (major class) were inhibited by the virus, whereas HRV 1a and 2 (minor class) were not.

The results described above indicate that the purified HRR can block the infectivity of rhinoviruses belonging to the major receptor class of rhinoviruses. The infectivity inhibition property of the receptor protein is correlated with its ability to bind to the virus, and is presumed to act by blocking the receptor binding site on the virus. This property of the receptor is manifested at low concentrations of the receptor protein, and indicates a high affinity of the receptor for the virus. The significance of these results is that the purified, soluble receptor could be used to inhibit the initiation or the spread of rhinovirus infections in vivo. The purified protein also provides a source of material from which smaller protein fragments and peptides could be derived which have the same activity as the intact receptor.

Purified protein was then subjected to limited or complete proteolytic degradation, peptides were purified by either reverse-phase chromatography, gel filtration, or SDS-PAGE, and then subjected to automated protein sequencing. These sequences were used to search protein sequence (NRFB and MIPSX) and DNA sequence (Genbank) databases. A match of all known peptide sequences determined from HRR protein was made. (Intercellular Adhesion Molecule-1 Simmons et al, "ICAM, An Adhesion Ligand of LFA-1, Is Homologous To The Neural Cell Adhesion Molecule of NCAM", *Nature,* 331,, 624–627 (1988)). ICAM was under investigation by other researchers because of its role in the adhesion of T lymphocytes to a variety of different cell types. It is hypothesized that ICAM (present on fibro-blasts, epithelial cells, leukocytes, and endo-thelial cells) interacts with a structure called LFA-1 (lymphocyte-function associated antigen-1) present on the surface of T lymphocytes, and is thereby responsible for the adhesion to these cell types.

We had determined the sequence of 106 amino acids of the rhinovirus receptor, and all 106 matched exactly the sequence of ICAM (out of a total of 507 amino acids predicted for the ICAM sequence). Other biochemical information supports the identity of HRR with ICAM. First, the primary mRNA translation product synthesized in an in vitro translation system has an apparent molecular weight of 55,000 daltons which is the same as ICAM. Secondly, the HRR protein species found in cells poisoned with tunicamycin, a specific inhibitor of asparagine-linked glycosylation, has an apparent molecular weight of 54,000 daltons, consistent with the removal of a signal sequence from the N-terminus of the protein. Third, partial digestion of core-glycosylated HRR protein indicates the presence of seven asparagine-linked carbohydrate groups, consistent with the presence of eight potential carbohydrate acceptor sequences (N-S/T) in the amino acid sequence of ICAM. Finally, the chromosome map position of HRR was determined to be human chromosome 19, identical to that determined for ICAM.

Since the complete nucleotide and amino acid sequence of ICAM has been determined, and there is substantial, if not overwhelming evidence that ICAM and the HRR are the same or very similar molecules, the complete amino acid sequence of the rhinovirus receptor is now known. The determination of this amino acid sequence, which is a partial chemical structure of this molecule, provides the ability to design and produce large amount of receptor protein, fragments, functional domains, and truncated versions, and analogs of receptor protein, and peptides that have inhibitory activity towards rhinovirus and coxsackie A virus infection. The complete amino acid sequence also provides information needed for biophysical and biochemical studies of rhinovirus-receptor interaction which will lead to the identification of crucial molecular contacts, which can be used for design of novel inhibitory molecules.

Since the ICAM molecule is a member of the immunoglobulin supergene family that maps to chromosome 19, (*Eur. J. Immunol.,* 15, 103–106 (1984) and since other picornaviruses, such as poliovirus and coxsackie virus, bind to receptors whose genes are located on chromosome 19, it is possible that ICAM can be used as a basis for the development of therapeutics to counter infections by those other picornaviruses as well. It is possible that ICAM or fragments thereof would be useful directly as therapeutics for other viruses and inflammatory diseases. Alternatively, knowledge of ICAM structure will be useful in the identification of the receptors of those viruses. Further, ICAM-1 is closely related to two adhesion proteins of the adult nervous system, neural cell adhesion molecule (NCAM) and myelin-associated glycoprotein (MAG) and a family of epithelial cell molecules including CEA, NCA, TM-CEA, and the pregnancy-specific B1-glycoproteins. NCAM, MAG and ICAM-1 each have five immunoglobulin-like domains, see Dustin et al "Supergene Families Meet In The Immune System", Commentary, Elsevier Publications, Cambridge, 1988. The relationship of the picornaviruses and the supergene family of ICAM, NCAM and MAG provide the basis of developing proteins, protein fragments, functional domains, analogs and mixtures thereof for inhibiting infectivity of this class of viruses.

Knowledge of the amino acid sequence, and information about the ICAM protein coupled with the knowledge of HHR and rhinovirus provide the basis for the following approaches to design protein fragments and analogs for treatment of rhinovirus infection and for treatment of inflammation.

Soluble forms of biologically active host cell protein could be used to inhibit virus infection, in contrast to the cell membrane bound receptor protein that normally facilitates the infection. Soluble forms of biologically active receptor protein, protein fragments, functional domains or analogs could include use of detergents as described supra. Alternatively, elimination of the C-terminus could render the protein(s) soluble. A biologically active tryptic fragment is a mixture of two species, one with an apparent molecular weight of 83,000 daltons and one of 90,000 daltons (relative to HRR of 95Kd). The N-terminus of both species is blocked, indicating that they start from residue 1 of the intact ERR molecule, and peptides are removed from C-termius: the largest possible fragment would be from residue 1 to residue 488. The downward shift in apparent molecular weight relative to intact HRR indicates a loss of >5,000 daltons, or 45 amino acid residues, which would place the new C-termini of fragments at positions proximal (N-terminal) to the transmembrane segment.

Examples of soluble fragments could include the entire extracellular domain (up to a.a. 480) or could include either/or both distinct parts of the extracellular domain (a.a. 1–200; 200–460) of the amino acid sequence of the receptor protein. It is further anticipated that smaller peptide fragments may provide biologically active analogs for inhibiting virus infection.

A full length cDNA clone of the HRR will be isolated from a cDNA library of Hel or other cells expressing the receptor by screening with oligonucleotides made from the published sequence of ICAM-1. Construction and expression of domain fragments of the HRR will be achieved using established recombinant DNA methodologies (Fisher et al, *Nature,* 331, 76–78 (1988); Hussey et al, *Nature,* 331, 78–81 (1988); Deen et al, *Nature,* 331, 82–86 (1988). A soluble extracellular domain will be made by cleaving a cDNA clone of the HRR coding sequence with ThaI which cute at position 37 in the signal peptide region and at position 1415, 12 amino acids before the start of the transmembrane domain. Synthetic oligonucleotide linkers will be added in a stepwise fashion to the 5' and 3' ends of the molecule to restore the signal peptide and initiator ATG at the N termnus and to introduce an in frame translational stop codon at the C-terminus. The position of the stop codon may be varied to produce alternative truncated forms of the molecule. Similarly, different infrequently cutting restriction enzymes will be used to insert stop codons in other regions of the molecule. Restriction enzyme sites will be included at the ends of the linkers to allow directional cloning into a variety of expression vectors. Oligonucleotide site directed mutagenesis, using conventional methods, will be used to introduce restriction enzyme sites where no convenient naturally occurring sites exist. Additionally, the polymerase chain reaction (PCA) technique will be used to produce specific DNA fragments encoding domains and other subregions of the molecule.

The approach described above will also be used to produce additional subfragments of the receptor such as the five immunoglobulin-like domains (residues 1–88, 89–185, 186–284, 285–385, 386453, Staunton et al, Cell 52, 925–933 (1988). Staunton et al. give a sequence for ICAM-1 ([SEQ ID NO:1] and FIG. 1) that begins numbering from Glu-3 of Simmons, supra). In this case appropriate signal sequences to direct protein secretion for the expression system being used will be included. Various expression systems will be used including viral promoters in mammalian cells (Cate et al, Cell, 45, 685–698 (1986), insect cells (Smith et al Pros. Acad. Sci. U.S.A., 82, 8404–8408 (1985); and *E. coli* (Skerra and Pluckthun, Science, 240, 1038–1041 (1988). Subfragments of the receptor produced in the above manner will be tested for the ability to bind major rhinovirus serotypes and to reduce virus infectivity. Expression of the extra-cellular domain as described above will also be used to derive sufficient quantities of the soluble receptor for structural studies such as X-ray crystallography.

Structural studies utilizing enzymatic and chemical fragmentation of nonreduced ICAM-1 have mapped three disulfide bonds out of the total of 7 potential pairs and have tentatively mapped two additional disulfide bonds. These results indicate disulfide bonds between C108 and C159, between C210 and C263, and between C305 and C344; cleavage at M64 with CNBr indicates that C21 and C25 pair C65 and C69, and model building based on the Ig-like fold indicates pairing C21 to C65 and C25 to C69. These data provide evidence to support a structural model of ICAM-1 with three N-terminal Ig-like domains (see FIG. 2.)

A series of cDNA's (tICAM's, or truncated ICAM's) were constructed from ICAM-1 cDNA to contain premature stop codons at amino acid positions 454, 284, or 185 of the mature protein (according to the sequence given in Staunton et al., Cell, 52, 925–933 (1988)) in order to produce secreted proteins progressively truncated from the C-terminus. The positions of the truncations were selected based on the predicted borders of the transmembrane domain (tICAM(1-453)), immunoglobulin-like domains 1+2+3 (tICAM(1-283)), and immunogobulin-like domains 1+2 (tICAM(1-183)) and immunoglobulin-like domain 1 (tICAM(1-88). The protein products of these genes are diagramed in FIG. 2. They were constructed by Polymerase Chain Reactions (PCR) using 5' and 3' oligonuceotide primers that overlap the ICAM-2 coding sequence and contain restriction enzyme sites; the 5' primer contained an additional EcoRl site and the 3' primers contained an additional translation stop codon and a BamI site. These DNA's were directionally cloned into the Bluescript-SK vector (Strategene), cut out with a HindIII/Xba digest. These genes and a control full length ICAM-1 cDNA were then directionally cloned into the expression vector CDM8 (Seed, et. al.) using the HindIII site at the 5' end and the xba site at the 3' end of the gene. These plasmids were transfected into COS cells using the DEAE-dextran technique and the cells cultured 72 hr. before assay. Surface expression was monitored by FACS using indirect immunofluorescence and a monoclonal antibody specific for ICAM-1. Secretion of ICAM-1 into the medium was monitored by metabolic labeling of cells for 7 hr. with [$^{35}$S] cysteine, followed by immunoabsorption of the culture supernatants with a monoclonal anti-ICAM-1-sepharose resin. The FACS analysis clearly showed surface expression df ICAM-1 in cells transfected with full-length ICAM-1; cells transfected with the CMS8 vector alone or with tICAM (1-453) showed no surface expression. When the material isolated from the metabolically-labeled culture supernatants were analysed by SDS-PAGE followed by fluorography, no ICAM-1 was observed in control or full length ICAM-1 transfectants, while an 80,000 dalton species was secreted by tICAM(1-453) transfectants, a 65,000 dalton protein was secreted by tICAM (1-283) transfectants, and a 43,000 dalton protein was secreted by tICAM (1-184) transfectants. When the same material was stained for protein by silver staining, it was apparent that the tICAM(1-453) was substantially pure. Stable transfectants were generated by transfecting the same cDNA's mixed with the gene for a selectable marker (thymidine kinase for mouse L cells dihydrofolate reductase for CHO cells) into mouse Ltk- cells or hamster CHO(dhfr-) cells and subjected to drug selection (HAT selection for Ltk- cells and methotrexate for CHO (dhfr-) cells). Surviving cells were cloned and culture supernatants from these cells were screened by a radioimmune assay in which MAb c78.5 was absorbed to microtliter dishes, purified ICAM-1 or culture supernatants incubated with the MAb-coated dishes, and then bound ICAM-1 detected by incubation with $^{135}$I-labeled MAb c78.4. Several L cell transfectants and one CHO cell transfectant secreting tICAM(1-453) and L cells expressing tICAM(1-183) were obtained. Expression was confirmed by metabolic labeling of cells followed by immunoabsorption of culture supernatants as described above.

tICAM(1-88) has been expressed in *E. Coli* using the OmpA secretion vector of Inoue. In this system, the OmpA signal peptide is fused to the N-terminu's of mature ICAM-1 protein. tICAM(1-88) and tICAM-183) have been placed into the OmpA vector; *E. coli* transformed with these vectors express protein products of the expected size as detected by western blotting of SDS-PAGE gels of cell extracts with anti-peptide antibodies to a sequence within domain 1 of ICAM-1.

Blocking studies with the panel of 6 MAbs to ICAM-1 (all of which inhibit virus binding to ICAM-1) indicate that there are two distinct epitopes defined by these antibodies, one defined by c78.4 (containing c78.1, c78.2, c92.1, and c92.5). Immunoprecipitation studies with proteolytic fragments of ICAM-1 and with in vitro translations of truncated ICAM-1 cDNA's indicate that both of these epitopes are contained within the first Ig-like domain.

In vitro virus-binding studies utilizing radiolabeled tICAM(1-453) and purified rhinovirus have indicated that it can bind to rhinovirus in solution.

Additional biologically active fragments will be evaluated utilizing overlapping sets of synthetic peptides of 10–20 residues corresponding to part or all of the HRR protein. The peptides will be made and individually tested for the ability to inhibit virus binding to receptor.

These peptide fragments could be direct copies of a portion of the rhinovirus receptor, or could contain sequences from non-contiguous regions of the receptor.

ICAM has been predicted, based on homology to NCAM, to be a member of the immunoglobulin gene superfamily. One would expect that the immunoglobulin-like domains in ICAM would have the basic "immunoglobulin fold", as has been shown for two other members of this family, beta-2-microglobulin and the HLA-A2 alpha-3 domain. This fold consists of a "beta-barrel" conformation consisting of two antiparallel beta-pleated sheets, one composed of three and one composed of four beta strands; a disulfide bond between two cysteine residues (separated by approximately 60 amino acids along the chain) connects the two sheets (Williams, A. F., *Immun. Today* 8, 298–303 (1987). Two of the disulfide bonds, those corresponding to domains 2 (C110-C161) and 3 (C212-C265), have been experimentally determined by us, providing support for the model. This model for the structure provides a basis for designing unique analogs that could mimic the virus binding site and be useful as receptor blockers. Each pair of antiparallel beta strands in the beta-barrel is linked by a hairpin turn of variable size; such turns or loops that protrude from secondary structures are often found to play roles in recognition of ligands (Lezczynski and Rose, *Science*. 224, 849–855 (1986). Such protruding structures may be of particular interest in the rhinovirus receptor, since the receptor binding site on the virus capsid is proposed to be in a recessed cavity. Using the sequence of the HRR, such turns and loops could be predicted based on a beta-barrel structure and produced as synthetic peptides with addition of novel cysteine residues at the N- and C-terminus of the peptides; a disulfide bond would then be formed between such residues on the same peptide to close the loop covalently (in contrast to the native protein, wherein the loop would be closed by noncovalent interactions between the adjacent beta-strands). Such peptides would have a conformation more analogous to the conformation in the native protein than a simple linear peptide, and would be tested for virus-binding activity.

Method of localizing the region or domain of the molecule responsible for virus-binding activity. Site-directed antibodies directed against specific portion of the HRR (predicted from a working model based on an immunoglobulin fold) could be produced by making synthetic peptides corresponding to selected regions of the protein, coupling such peptides to larger carrier proteins, and immunizing rabbits or other animals with such conjugates by standard methodology. Such antibodies could be tested for the ability to inhibit virus binding; inhibition with a subset of such antibodies would direct attention to specific domains or parts of domains.

Specific reactive groups on some amino acid residues on the receptor protein can be chemically modified under non-denaturing conditions. As a consequence of the modification of some residues virus-binding ability may be lost. By the use of radioactive tracers in the modifying reagent, the modification of some amino acid residues may be correlated with loss of binding activity, implicating those groups in recognition. This would direct attention towards a specific part of the molecule or a specific amino acid residue as playing a specific role in virus binding. Such residues could then be experimentally modified in in vitro mutagenesis experiments. As an example, it has been found that labelling HRR with radioactive Bolton/Hunter reagent (an N-hydroxysuccinimide ester, which specifically modifies N-termini and lysine residues) substantially reduces its ability to bind to rhinovirus.

Determination of the three dimensional structure of the virus-binding domain of the HRR by X-ray crystallography and/or Nuclear Magnetic Resonance. Using the three-dimensional coordinates of HRV14 (from the Brookhaven Data Bank), find the optimal "docking" of the two molecules by computer graphics methodology. The structure of the "docked" complex could then be used to refine and improve the properties of the protein or peptide fragment of the receptor. Examples of such improvements would be: (1) increasing the affinity of virus-binding reaction; (2) producing a smaller molecule; and (3) deleting or damaging other regions of the molecule, such as that needed for binding to LFA-1. If the binding site for LFA-1 is on a different domain, the domain could be deleted. Alternatively, if the binding site for LFA-1 is on the virus-binding domain, site directed mutagenesis of specific amino acids could be used to inhibit the ability to binding.

Key residues of the receptor involved in virus binding will be determined by oligonucleotide site directed mutagenesis. For example, pools of mutants produced by saturation mutagenesis will be screened by the method of Peterson and Seed (*Cell*, 54, 65–72 (1988), using either HRV14 or monoclonal antibody/complement killing as the negative selection, and a rabbit polyclonal antibody as the positive selection. Synthetic peptides corresponding to regions of the molecule identified in this way will be made and tested for virus bending and the ability to reduce infectivity.

Pharmaceutical preparations of proteins, protein fragments, functinal domain and analogs have an application in a plurality of diseases. With the Knowledge that HRV and LFA-1 both bind to ICAM it is anticipated that analogs of ICAM could be designed that bind to rhinovirus and thereby inhibit rhinovirus infection, but which do not disrupt the interaction of ICAM and LFA-1. Alternatively, mitogenesis of selected residues (amino acids) will be made based on structural predictions and biochemical structure.

Again with the knowledge that ICAM and HRR are the same molecule, it is anticipated that it may have application in fragments, functional domains or analogs of LFA-1 could be utilized to disrupt interactions between HRR and rhinovirus and thereby treat rhinovirus infections.

HRR or fragments of it may have application in the disruption of interactions between ICAM and LFA-1, which could be useful for the treatment of inflammation.

Peptides derived from the known capsid proteins of rhinovirus could be useful for the disruption of interactions between ICAM and LFA-1, which could be useful for the treatment of inflammation. Carbohydrate groups that are not necessary for biological activity will be removed to enhance production of peptides in bacteria.

Site-directed mutagenesis of cystines may be useful to limit refolding to biologically active conformations.

What is claimed is:

1. A method of inhibiting infection of a host cell by human rhinovirus (HRV) in tissues susceptible to such infection, said method comprising contacting said HRV with a polypeptide comprising a fragment of human rhinovirus major receptor (HRR) [SEQ ID NO:1], said fragment comprising the HRV binding site and being selected from the group consisting of the following sets of HRR domains:

I and II (tICAM(1-185)),
I, II, and III (tICAM(1-284)),
I, II, III, and IV (tICAM(1-385)), or
I, II, III, IV, and V (tICAM(1453))

said contact being under conditions which permit said HRV to bind to said polypeptide, whereby said HRV is inhibited from infecting said host cell.

2. The method of claim 1 wherein said polypeptide comprises tICAM(1-185).

3. The method of claim 1 wherein said polypeptide comprises tICAM(1-284).

4. The method of claim 1 wherein said polypeptide comprises tICAM(1-385).

5. The method of claim 1 wherein said polypeptide comprises tICAM(1-453).

6. The method of claim 1 wherein said polypeptide is applied by appropriate contact with those areas of the body susceptible to infection by HRV.

7. The method of claim 6 wherein said polypeptide is applied as an intranasal spray.

8. A method of inhibiting infection of a host cell by human rhinovirus (HRV) in tissues susceptible to such infection, wherein said virus is capable of binding to the human rhinovirus receptor (ICAM-1) expressed on the surface of said host cell in said tissue, said method comprising the steps of:

(a) expressing in a suitable expression system in a suitable host a nucleotide sequence coding for a polypeptide comprising ICAM-1 [SEQ ID NO:1] or a fragment thereof, which fragment is capable of binding to said HRV and reducing infectivity thereof;

(b) isolating and purifying the resulting polypeptide; and (c) contacting said HRV with said polypeptide under conditions which permit said virus to bind to said polypeptide, whereby said virus is inhibited from infecting said cell.

9. The method of claim 8, wherein said nucleotide sequence codes for a polypeptide comprising amino acids 1-185 of ICAM-1.

10. The method of claim 8, wherein said nucleotide sequence codes for a polypeptide comprising amino acids 1-284 of ICAM-1.

11. The method of claim 8, wherein said nucleotide sequence codes for a polypeptide comprising amino acids 1-385 of ICAM-1.

12. The method of claim 8, wherein said nucleotide sequence codes for a polypeptide comprising amino acids 1453 of ICAM-1.

13. The method of claim 8, wherein said nucleotide sequence comprises the OmpA vector.

14. The method of claim 8, wherein the host cell is a eukaryotic cell capable of secreting said polypeptide.

15. The method of claim 8, wherein said eukaryotic cell is mammalian.

16. The method of claim 8 wherein said host cell is a prokaryotic cell capable of expressing said polypeptide.

17. The method of claim 8, wherein said polypeptide is applied by appropriate contact with those areas of the body susceptible to infection by HRV.

18. The method of claim 8, wherein said polypeptide is applied as an intranasal spray.

19. A method for inhibiting binding of human rhinovirus to human rhinovirus receptor [SEQ ID NO:1] in a host cell in tissue susceptible to rhinovirus infection, comprising the step of contacting the virus with a polypeptide comprising the HRV binding domain of HRR; which polypeptide is capable of binding to rhinovirus of the major receptor class and reducing infectivity thereof, said contact being under conditions which permit said rhinovirus to bind to said polypeptide.

* * * * *

SEQUENCE LISTING

<160> NUMBER OF SEQ ID NOS: 1

<210> SEQ ID NO 1
<211> LENGTH: 507
<212> TYPE: PRT
<213> ORGANISM: Homo sapiens

<400> SEQUENCE: 1

```
Asn Ala Gln Thr Ser Val Ser Pro Ser Lys Val Ile Leu Pro Arg Gly
1               5                   10                  15

Gly Ser Val Leu Val Thr Cys Ser Thr Ser Cys Asp Gln Pro Lys Leu
            20                  25                  30

Leu Gly Ile Glu Thr Pro Leu Pro Lys Lys Glu Leu Leu Leu Pro Gly
        35                  40                  45

Asn Asn Arg Lys Val Tyr Glu Leu Ser Asn Val Gln Glu Asp Ser Gln
    50                  55                  60

Pro Met Cys Tyr Ser Asn Cys Pro Asp Gly Gln Ser Thr Ala Lys Thr
65                  70                  75                  80

Phe Leu Thr Val Tyr Trp Thr Pro Glu Arg Val Glu Leu Ala Pro Leu
                85                  90                  95

Pro Ser Trp Gln Pro Val Gly Lys Asn Leu Thr Leu Arg Cys Gln Val
            100                 105                 110

Glu Gly Gly Ala Pro Arg Ala Asn Leu Thr Val Val Leu Leu Arg Gly
        115                 120                 125

Glu Lys Glu Leu Lys Arg Glu Pro Ala Val Gly Glu Pro Ala Glu Val
    130                 135                 140

Thr Thr Thr Val Leu Val Arg Arg Asp His His Gly Ala Asn Phe Ser
145                 150                 155                 160

Cys Arg Thr Glu Leu Asp Leu Arg Pro Gln Gly Leu Glu Leu Phe Glu
                165                 170                 175

Asn Thr Ser Ala Pro Tyr Gln Leu Gln Thr Phe Val Leu Pro Ala Thr
            180                 185                 190

Pro Pro Gln Leu Val Ser Pro Arg Val Leu Glu Val Asp Thr Gln Gly
        195                 200                 205

Thr Val Val Cys Ser Leu Asp Gly Leu Phe Pro Val Ser Glu Ala Gln
    210                 215                 220

Val His Leu Ala Leu Gly Asp Gln Arg Leu Asn Pro Thr Val Thr Tyr
225                 230                 235                 240

Gly Asn Asp Ser Phe Ser Ala Lys Ala Ser Val Ser Val Thr Ala Glu
                245                 250                 255

Asp Glu Gly Thr Gln Arg Leu Thr Cys Ala Val Ile Leu Gly Asn Gln
            260                 265                 270

Ser Gln Glu Thr Leu Gln Thr Val Thr Ile Tyr Ser Phe Pro Ala Pro
        275                 280                 285

Asn Val Ile Leu Thr Lys Pro Glu Val Ser Glu Gly Thr Glu Val Thr
    290                 295                 300

Val Lys Cys Glu Ala His Pro Arg Ala Lys Val Thr Leu Asn Gly Val
305                 310                 315                 320

Pro Ala Gln Pro Leu Gly Pro Arg Ala Gln Leu Leu Leu Lys Ala Thr
                325                 330                 335

Pro Glu Asp Asn Gly Arg Ser Phe Ser Cys Ser Ala Thr Leu Glu Val
            340                 345                 350

Ala Gly Gln Leu Ile His Lys Asn Gln Thr Arg Glu Leu Arg Val Leu
```

-continued

```
                355                 360                 365
Tyr Gly Pro Arg Leu Asp Glu Arg Asp Cys Pro Gly Asn Trp Thr Trp
    370                     375                 380

Pro Glu Asn Ser Gln Gln Thr Pro Met Cys Gln Ala Trp Gly Asn Pro
385                 390                 395                 400

Leu Pro Glu Leu Lys Cys Leu Lys Asp Gly Thr Phe Pro Leu Pro Ile
                405                 410                 415

Gly Glu Ser Val Thr Val Thr Arg Asp Leu Glu Gly Thr Tyr Leu Cys
                420                 425                 430

Arg Ala Arg Ser Thr Gln Gly Glu Val Thr Arg Glu Val Thr Val Asn
            435                 440                 445

Val Leu Ser Pro Arg Tyr Glu Ile Val Ile Ile Thr Val Val Ala Ala
    450                 455                 460

Ala Val Ile Met Gly Thr Ala Gly Leu Ser Thr Tyr Leu Tyr Asn Arg
465             470                 475                 480

Gln Arg Lys Ile Lys Lys Tyr Arg Leu Gln Gln Ala Gln Lys Gly Thr
                485                 490                 495

Pro Met Lys Pro Asn Thr Gln Ala Thr Pro Pro
            500                 505
```